US011357271B2

United States Patent
Mason

(10) Patent No.: US 11,357,271 B2
(45) Date of Patent: Jun. 14, 2022

(54) LEOTARD WITH BUILT IN COMPRESSION

(71) Applicant: Faith Elizabeth Mason, San Jose, CA (US)

(72) Inventor: Faith Elizabeth Mason, San Jose, CA (US)

( * ) Notice: Subject to any disclaimer, the term of this patent is extended or adjusted under 35 U.S.C. 154(b) by 17 days.

(21) Appl. No.: 16/659,517

(22) Filed: Oct. 21, 2019

(65) Prior Publication Data

US 2020/0120999 A1    Apr. 23, 2020

Related U.S. Application Data

(60) Provisional application No. 62/749,402, filed on Oct. 23, 2018.

(51) Int. Cl.
| | | |
|---|---|---|
| *A41D 13/00* | (2006.01) | |
| *A41C 1/02* | (2006.01) | |
| *A41D 31/18* | (2019.01) | |

(52) U.S. Cl.
CPC ............ *A41D 13/0015* (2013.01); *A41C 1/02* (2013.01); *A41D 31/18* (2019.02); *A41D 2400/38* (2013.01); *A41D 2600/10* (2013.01)

(58) Field of Classification Search
CPC ............ A41D 2400/38; A41D 13/0015; A41D 2600/10; A41D 31/125; A41D 31/185; A41C 1/02; A41C 1/06
USPC ................................ 450/124, 131, 115, 116
See application file for complete search history.

(56) References Cited

U.S. PATENT DOCUMENTS

| | | | | |
|---|---|---|---|---|
| 2,092,900 A | * | 9/1937 | Wipperman ............. | A41C 1/02 450/116 |
| 2,966,912 A | * | 1/1961 | Murdock ............... | A41C 1/003 450/116 |
| 5,888,118 A | * | 3/1999 | Kishi ....................... | A41D 1/14 450/122 |
| 7,395,557 B1 | * | 7/2008 | Ledyard .................. | A41B 9/06 2/113 |
| 8,568,195 B1 | * | 10/2013 | Schindler ................. | A41D 1/18 450/30 |
| 2009/0171259 A1 | * | 7/2009 | Soerensen ............. | A61F 13/148 602/67 |
| 2011/0107502 A1 | * | 5/2011 | Dalhausser ............. | A61F 13/08 2/456 |
| 2014/0090142 A1 | * | 4/2014 | Waller ............... | A41D 13/0015 2/67 |
| 2014/0148741 A1 | * | 5/2014 | Moran .................... | A61F 13/08 601/84 |
| 2015/0007374 A1 | * | 1/2015 | Larson .................. | A41D 15/00 2/67 |

(Continued)

FOREIGN PATENT DOCUMENTS

| | | | | |
|---|---|---|---|---|
| GB | 2560309 A | * | 9/2018 | ............... A41C 1/02 |
| WO | WO-2015139076 A1 | * | 9/2015 | ............... A41C 1/06 |

*Primary Examiner* — Jameson D Collier
*Assistant Examiner* — Matthew R Marchewka
(74) *Attorney, Agent, or Firm* — Knobbe Martens Olson & Bear, LLP

(57) ABSTRACT

A compression leotard is provided to aid the performance of athletes where compression panels are incorporated to mimic and support specific muscle groups, while aiding muscle metabolism and protecting joints. Panels are sized and positioned to apply a targeted pressure over a known area, such as hips, shoulders and spine, to reduce inflammation and stress on joints in the body core.

20 Claims, 20 Drawing Sheets

(56) References Cited

U.S. PATENT DOCUMENTS

| | | | |
|---|---|---|---|
| 2015/0038052 A1* | 2/2015 | Hays | A41C 1/12 |
| | | | 450/154 |
| 2015/0150309 A1* | 6/2015 | Huang | A41C 1/02 |
| | | | 450/116 |
| 2015/0245670 A1* | 9/2015 | Angelino | A41C 1/003 |
| | | | 450/7 |
| 2016/0015088 A1* | 1/2016 | Hendrickson | A41D 1/21 |
| | | | 450/95 |
| 2016/0076175 A1* | 3/2016 | Rock | A61F 13/08 |
| | | | 66/171 |
| 2017/0006925 A1* | 1/2017 | Priest | A41C 1/06 |
| 2017/0295861 A1* | 10/2017 | Trodden | A41D 13/0015 |
| 2018/0020746 A1* | 1/2018 | Wyner | A41D 31/125 |
| | | | 2/237 |
| 2019/0059465 A1* | 2/2019 | Zimmer | A41D 27/02 |
| 2019/0142081 A1* | 5/2019 | Kingsbury | A41D 1/08 |
| | | | 2/69 |
| 2019/0246717 A1* | 8/2019 | Fischer | A41D 1/22 |

* cited by examiner

LEOTARD WITH BUILT IN COMPRESSION

CROSS-REFERENCE TO RELATED APPLICATION

This application claims benefit under 35 U.S.C. 119(e) to U.S. Provisional Patent Application No. 62/749,402, filed Oct. 23, 2018, the entire disclosure of which is hereby incorporated by reference herein in its entirety. Any and all priority claims identified in the Application Data Sheet, or any corrections thereto, are hereby incorporated by reference under 37 CFR 1.57.

TECHNICAL FIELD

This application relates to athletic apparel, such as a unitards or leotards, comprising a compression fabric for supporting and aiding in muscular metabolism in joints of athletes such as gymnasts. The athletic apparel of the present invention may further comprise a means for absorbing body fluid leaked during strenuous exercise.

DISCUSSION OF THE RELATED ART

Athletes push the limits of what their bodies are capable of. Training in their sport often results in fractured bones, strained and torn ligaments, muscle inflammation and trauma to joints and discs as the training demands exceed the capacity of the body to endure. Elite athletes train and perform at the very edge of injury, with insufficient recovery time, often resulting in chronic fatigue, inflammation and pain.

Joints move when skeletal muscles contract. Skeletal muscles are arranged in antagonist pairs to provide bidirectional movement. Muscles contract when a signal transmitted by the brain reaches neurons within the muscle resulting in a release of calcium. Contractions are powered by adenosine triphosphate (ATP) which is generated either by aerobic (where oxygen is used by cells to convert fats, proteins and carbohydrates into energy (ATP) or anaerobic (where carbohydrates are used exclusively) processes. Both processes create metabolites that must be flushed from the tissue to allow the processes to continue. Buildup of metabolites can result in inflammation—and reduce local circulation—resulting in insufficient ability of the muscle to contract. Reduced local circulation can also result in depriving the area of oxygen and fuel. Oxygen, electrolytes and nutrients are delivered to tissue via the vascular system which transfers to the interstitial fluid (lymph) that supply individual cells. That same interstitial fluid (lymph) is the means of transport of metabolites away from cells. Interstitial fluid is moved by the contraction of skeletal muscles. Muscle fatigue—the reduced ability of a muscle to contract—can result in several affects: fatigue in a single muscle of an antagonist pair can result in the joint being unequally loaded and end in cartilage, ligament or disc damage; muscle fatigue in a region results in lower interstitial fluid flow and slows metabolic response and recovery.

SUMMARY

An aspect is directed to leotard to be worn by a user. The leotard having an upper portion which is to be worn around at least the chest of the user, a lower portion which is to be worn over at least the crotch of the user, and a compression system disposed between and attaching the upper portion to the lower portion, the compression system comprising a textile having a compression level greater than compression levels of the upper portion and the lower portion.

A variation of the aspect above is, wherein the compression level of the compression system is at least twice as great as the compression levels of the upper portion and the lower portion.

A variation of the aspect above is, wherein the upper portion and the lower portion each comprise tricot fabric.

A variation of the aspect above is, wherein the compression level of the compression system is 15-20 mmHg.

A variation of the aspect above is, wherein the compression system is to be worn around the waist of the user.

A variation of the aspect above is, wherein a width of the middle band is 7 inches.

A variation of the aspect above is, wherein the compression system comprises a zipper configured to move between an open position and a closed position, a circumference of the compression system being greater when the zipper is in the open position than when the zipper is in the closed position.

A variation of the aspect above is, wherein at least a region of the lower portion comprises an absorber system, the absorber system comprising an inner layer comprising a moisture wicking material and an outer layer comprising a protective lining.

Another aspect is directed to a leotard to be worn by a user. The leotard having an upper portion which is to be worn around at least the chest of the user and comprising spandex, a lower portion which is to be worn over at least the crotch of the user and comprising spandex, and a compression system disposed between and attaching the upper portion to the lower portion, the compression system having a percentage of spandex that is at least twice as great as a percentage of spandex in each of the upper portion and the lower portion.

A variation of the aspect above is, wherein the percentage of spandex in the compression system is 55.

A variation of the aspect above is, wherein the percentage of spandex in the upper portion and the lower portion is 19%.

A variation of the aspect above is, wherein the compression system comprises 55% spandex by weight.

A variation of the aspect above is, wherein the upper portion and the lower portion each comprise 19% spandex.

Another aspect is directed to a garment to be worn about at least the torso and the crotch of a user. The garment having an upper portion which is to be worn around at least the chest of the user, a lower portion which is to be worn over at least the crotch of the user, and a compression system disposed between the upper portion and the lower portion, the compression system covering at least a portion of the torso and comprising a textile having a compression level of 10-20 mmHg.

A variation of the aspect above is, wherein the compression system is to cover the oblique muscles of the user.

A variation of the aspect above further comprises an upper panel attached to at least the upper portion, the upper panel to be worn over at least portions of the upper back and the shoulder of the user.

A variation of the aspect above is, wherein a diameter of the compression system is contoured inward 2-3 inches relative to the upper portion and the lower portion.

A variation of the aspect above is, wherein the compression system comprises a zipper configured to move between an open position and a closed position.

A variation of the aspect above is, wherein at least a region of the lower portion comprises an absorber system, the absorber system comprising an inner layer comprising a moisture wicking material and an outer layer comprising a protective lining.

A variation of the aspect above is, wherein the compression system comprises an inner layer and an outer layer, each of the inner and outer layers comprising a textile having a compression level of 10-20 mmHg.

Another aspect is directed to a method for manufacturing a leotard. The method includes forming an upper textile portion, a lower textile portion, and a compression system, the compression system comprising a textile having a compression level greater than compression levels of the upper textile portion and the lower textile portion, and combining the upper textile portion, the lower textile portion, and the compression system so that the compression system is disposed between and attaching the upper portion to the lower portion.

A variation of the aspect above is, wherein the upper portion is to be worn around at least the chest of the user, and wherein the lower portion is to be worn over at least the crotch of the user.

A variation of the aspect above is, wherein forming the upper textile portion, the lower textile portion, and the compression system includes cutting shapes of the upper textile portion and the lower textile portion from a textile comprising a first wt. % of spandex, and cutting a shape of the compression system from a textile comprising a second wt. % of spandex, the second wt. % being greater than the first wt. %.

A variation of the aspect above is, wherein combining the upper textile portion, the lower textile portion, and the compression system comprises sewing both the upper textile portion and the lower textile portion to the compression system along respective seams.

BRIEF DESCRIPTION OF THE DRAWINGS

The present inventions are described with reference to the accompanying drawings, in which like reference characters reference like elements, and wherein.

DETAILED DESCRIPTION

Compressing the tissue surrounding joints by taping, use of compression bandages and braces which limit the range of motion and adds structural rigidity has long been used to protect joints on the extremities (wrists, ankles, knees and elbows). Supporting and protecting joints in the core (shoulders, hips and back) have been more difficult. Compressing the tissue has the added benefit of not allowing interstitial fluid to pool, and aids in local muscle metabolism. Compression by means of a brace or elastomeric fabric may only provide even compression of the tissue when the joint is in the neutral position. When the joint is flexed, it preferentially compresses the tissue of a single antagonist pair, allowing for a differential rate of interstitial fluid flow. Taping may improve the level of compression in tissue surrounding a joint as multiple layers can be applied that come into play as the joint is flexed. Multiple layers of tape, however can become rigid and limit flexibility, and if not applied properly can overstress a joint causing injury. Applying the tape in this fashion also requires skill.

Purpose built appliances are also available for primary joints. Strap on back supports and shoulder braces are limited in functionality and are generally not practical for gymnasts. What is needed is a means to provide support and aid in muscular metabolism in joints (e.g., hips, shoulder and back) of athletes.

Embodiments disclosed herein addresses one or more of these needs. In certain embodiments, the garment incorporates medical grade compression fabric. This fabric is sized and positioned within the apparel to mimic and aid specific muscle groups to reduce fatigue and protect joints. For example, in certain embodiments, a panel of compression fabric is disposed in a gym leotard over the abdominal external oblique. In certain embodiments, the panel applies appropriate compression to maintain muscle metabolism and provide an additional structural support resulting in reduced pressure on the lumbar. In certain embodiments, the panel can be applied strategically to aid muscle groups, without reducing joint flexibility or athletic performance.

Figure 1:
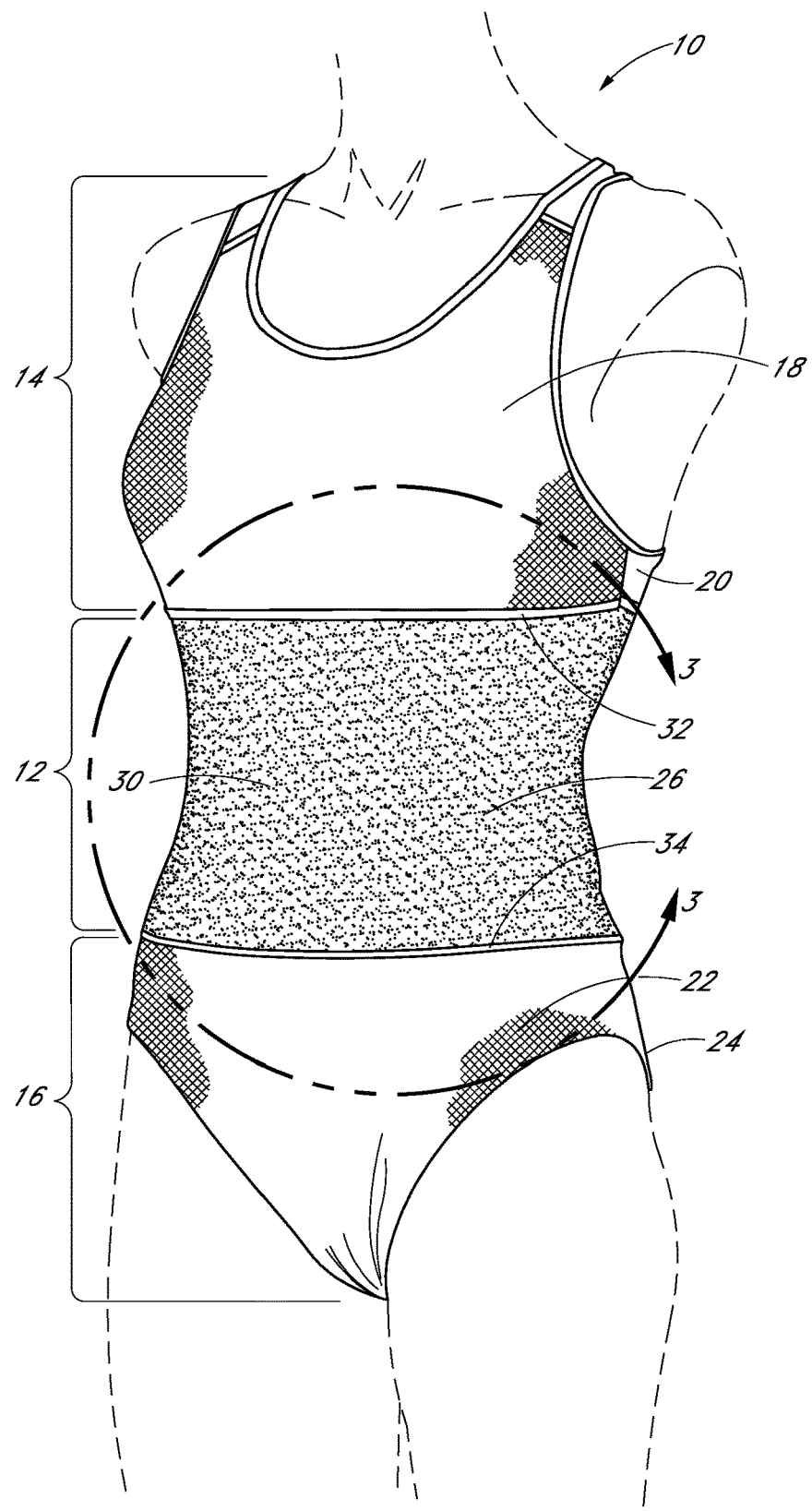
FIG. 1 is a front perspective view of a leotard having a compression system disposed around the waist of the user according to a preferred embodiment of the present invention.
Figure 2:
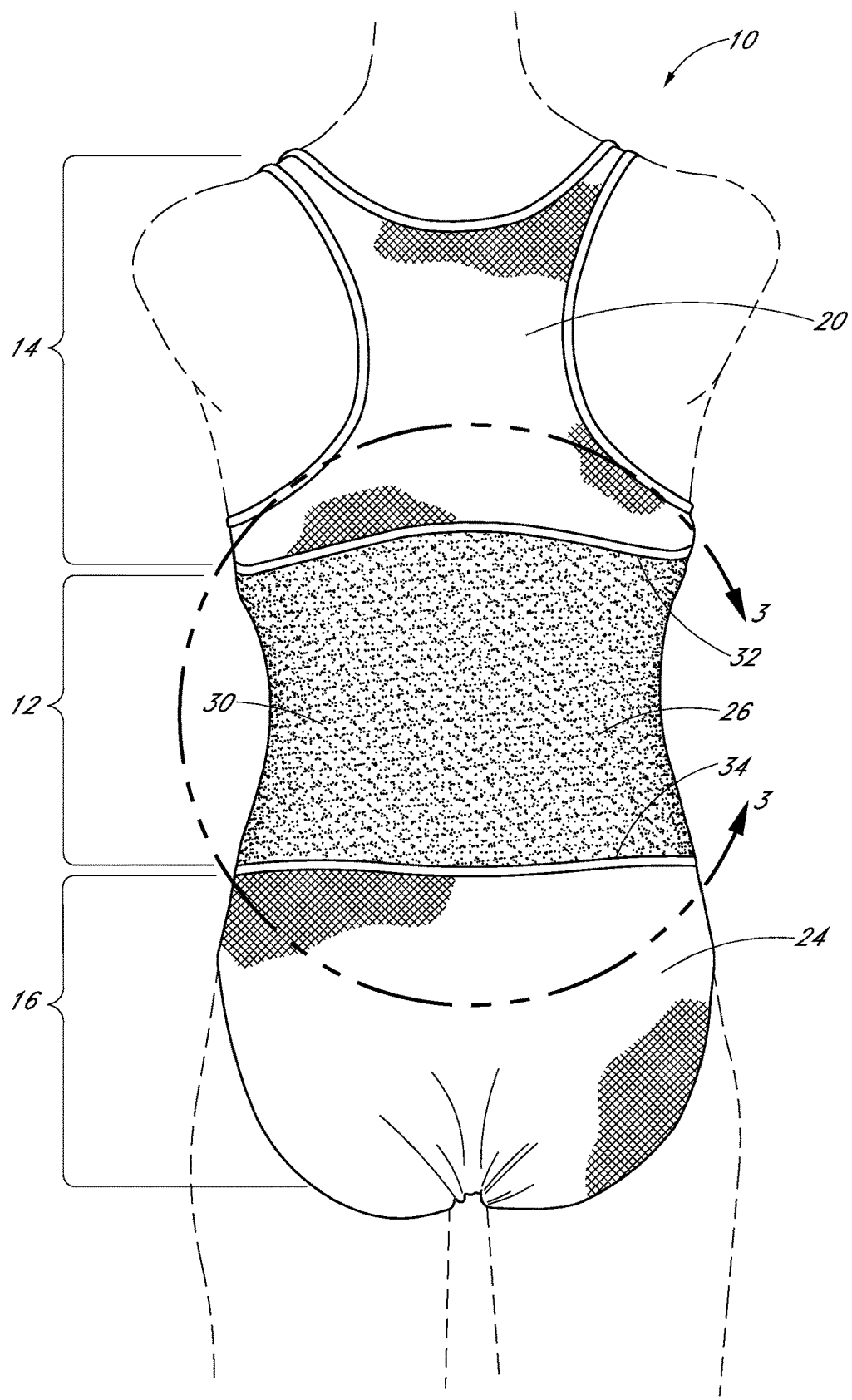
FIG. 2 is a back perspective view of the leotard from FIG. 1 showing one or more panels of the compression system.
Figure 3:
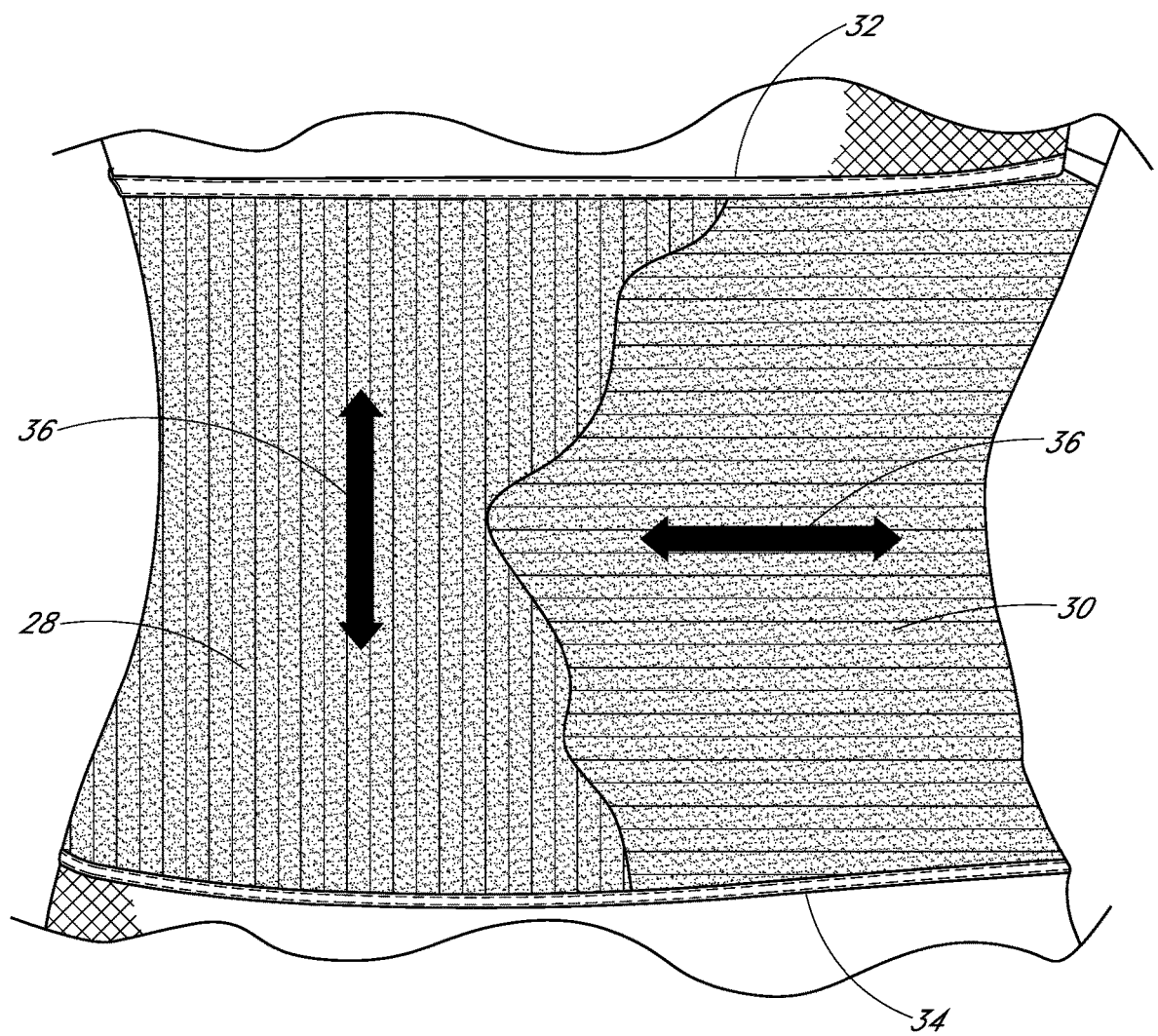
FIG. 3 is a cut-away view of the leotard from FIGS. 1 and 2 showing overlapping inner and outer layers of the one or more panels of the compression system.

FIG. 1 is a front perspective view of a garment 10 having a compression system 12 disposed around the waist of the user according to a preferred embodiment of the present invention. FIG. 2 is a back perspective view of the garment 10 from FIG. 1 showing one or more panels 26 of the compression system 12. FIG. 3 is a cut-away view of the garment 10 from FIGS. 1 and 2 showing overlapping inner and outer layers 28, 30 of the one or more panels 26 of the compression system 12. It will be understood that the compression system 12 can be incorporated into any style of garment including leotards, unitards, or body suits known to those of ordinary skill in the art. Further, it will be understood that the compression system 12 is preferably located in a predetermined pattern corresponding to one or more regions of the user's body. The waist is only one exemplary region of the user's body.

In certain embodiments, the garment 10 is a one-piece leotard that covers the body from the crotch to the shoulder. For example, the garment 10 in FIG. 1 is a leotard. In certain embodiments, the garment 10 comprises an upper portion 14 which is to be worn around at least the chest of the user. In certain embodiments, the garment 10 comprises a lower portion 16 which is to be worn over at least the crotch of the user.

The upper portion 14 and the lower portion 16 can each comprise one or more panels of fabric. For example, the upper portion 14 can comprise at least a front panel 18 and a back panel 20. In certain embodiments, the front panel 18 and the back panel 20 are sewn together to form the upper portion 14. Similarly, the lower portion 16 can comprise at least a front panel 22 and a back panel 24 that are sewn together to form the lower portion 16. Each of the upper and lower portions 14, 16 can be formed using seamless construction.

Figure 4:
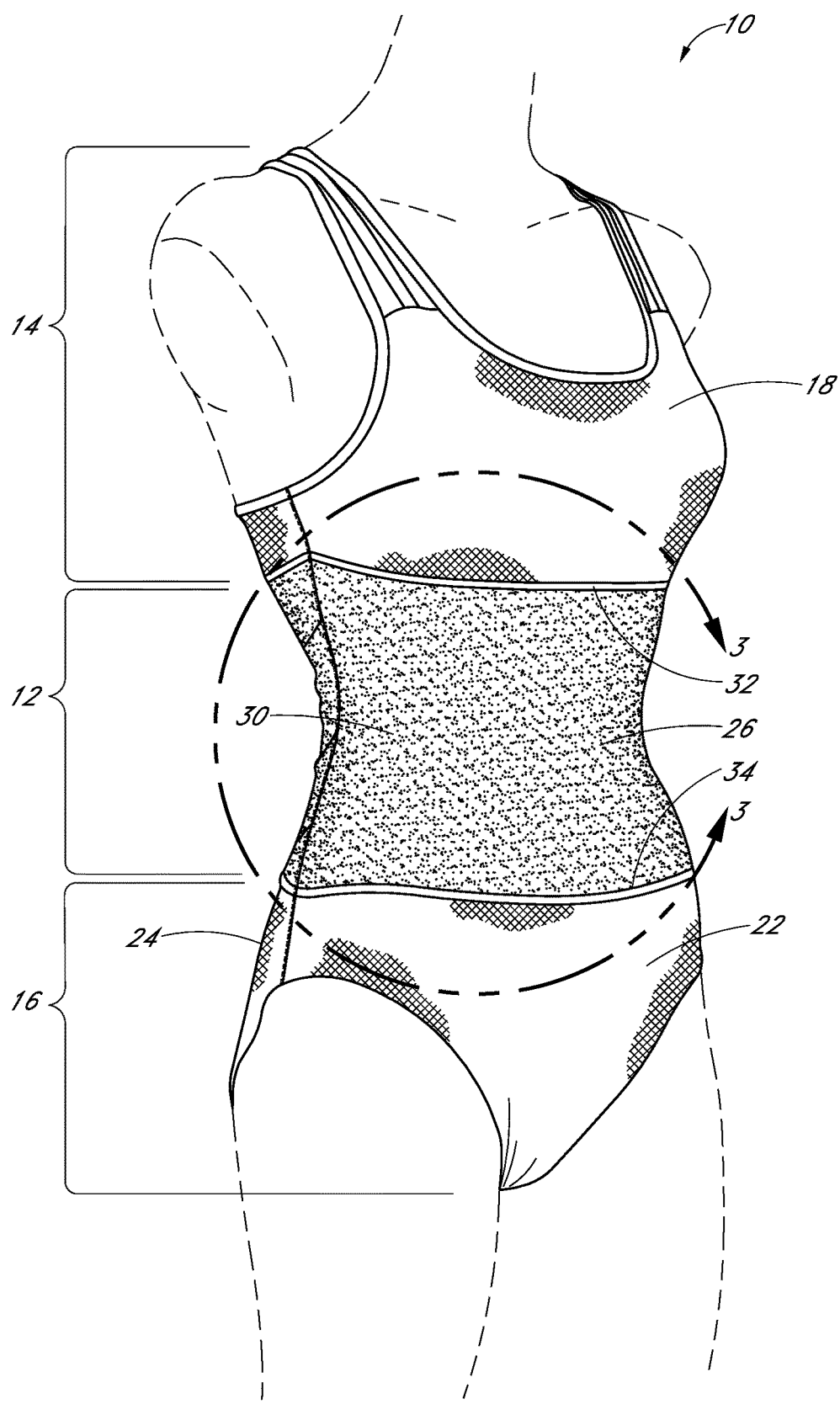
FIG. 4 is a front perspective view of another embodiment of a leotard having a compression system disposed around the waist of the user.
Figure 5:
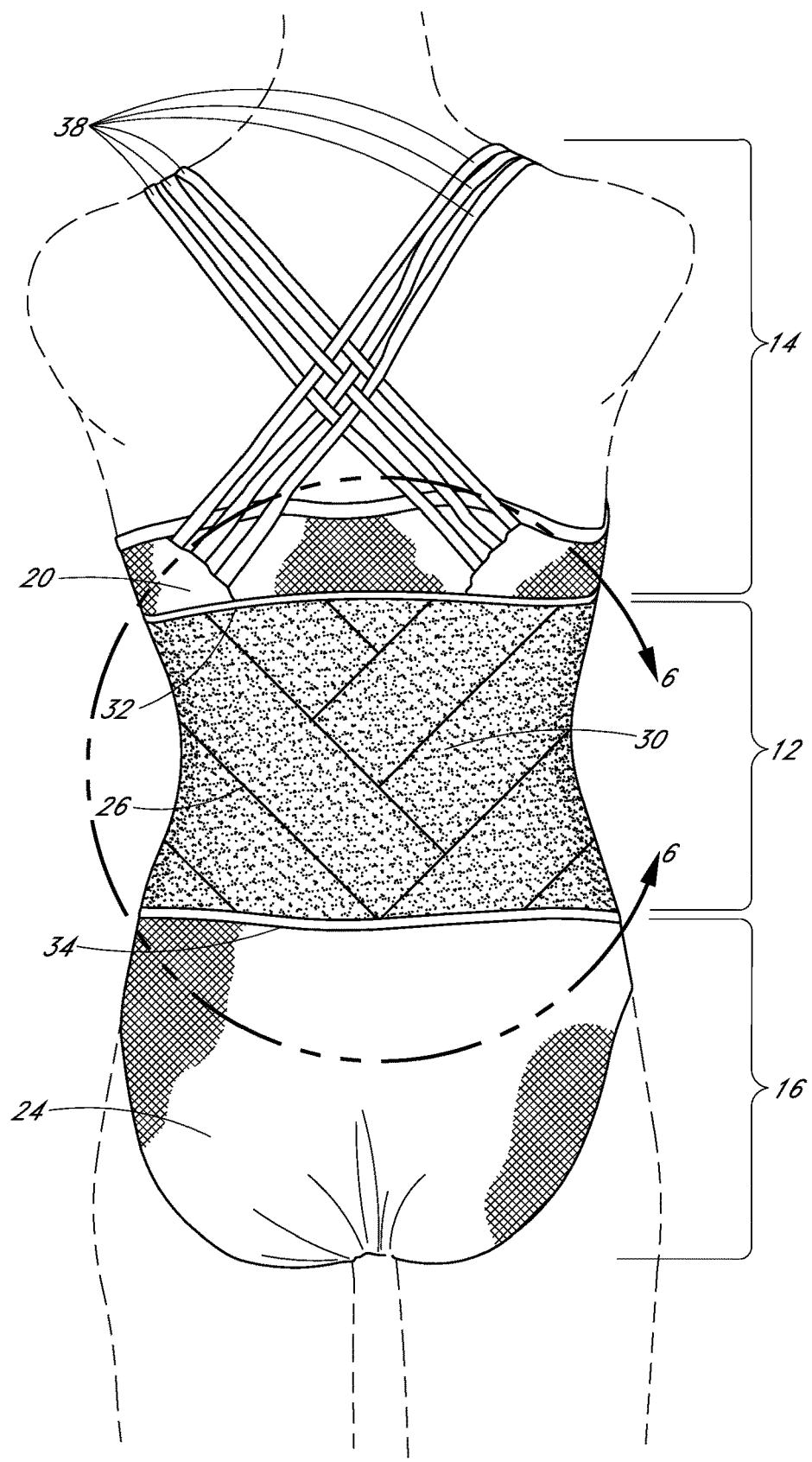
FIG. 5 is a back perspective view of the leotard from FIG. 4 showing an arrangement of the one or more panels of the compression system along with one or more straps.
Figure 6:
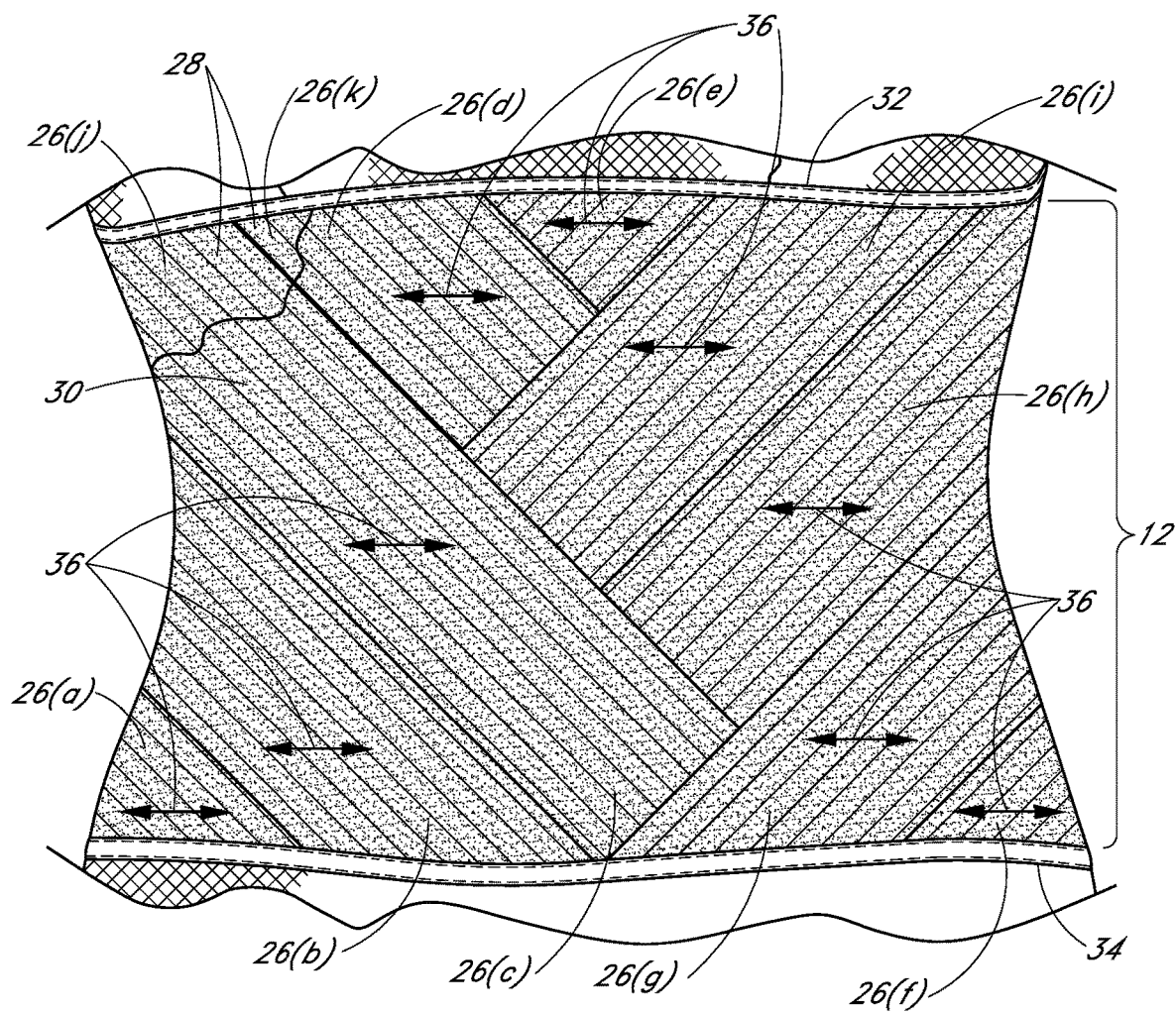
FIG. 6 is a partial view of the leotard from FIGS. 5 and 9 showing the one or more panels of the compression material.

FIG. 4 is a front perspective view of another embodiment of a garment 10 having a compression system 12 disposed around the waist of the user. FIG. 5 is a back perspective view of the garment 10 from FIG. 4 showing an arrangement of the one or more panels 26 of the compression system 12 along with one or more straps 38. FIG. 6 is a partial view of the garment from FIG. 5 showing the one or more panels 26 (a)-(i) of the outer layer 30 and one or more panels 26 (j), (k), . . . of the inner layer 28. For convenience, only 26 (j) and 26 (k) are illustrated in FIG. 5. Of course, each layer 28, 30 may include any number of panels 26. The one or more panels 26 are arranged at 45 degree angles. Of course the angle is not limited to 45 degrees, and can be any other angle including, for example 30 degrees and 60 degrees. Further, in certain embodiments, the garment 10 comprises at least one panel 26 that is at a different angle that another panel 26 of the garment 10. In certain embodiments, each of the one or more panels 26 comprises two layers of compression material. In certain embodiments, the inner and outer layers 28, 30 are sewn on top of each other to form each of the panels 26.

Figures 7, 8:
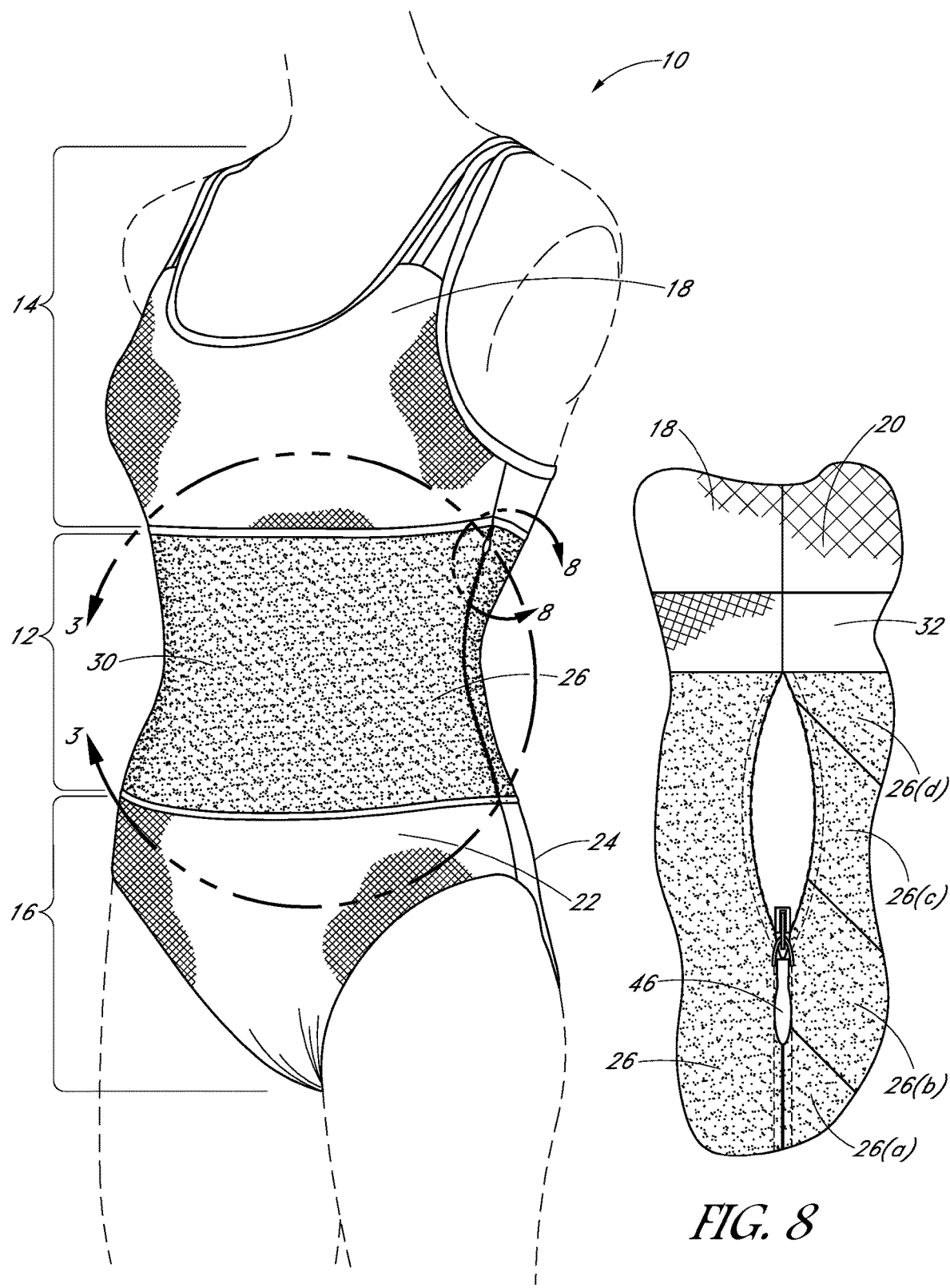
FIG. 7 is a front perspective view of another embodiment of a leotard having a zipper in the compression system.
FIG. 8 is a partial view of the leotard from FIG. 7 showing the zipper.
Figure 9:
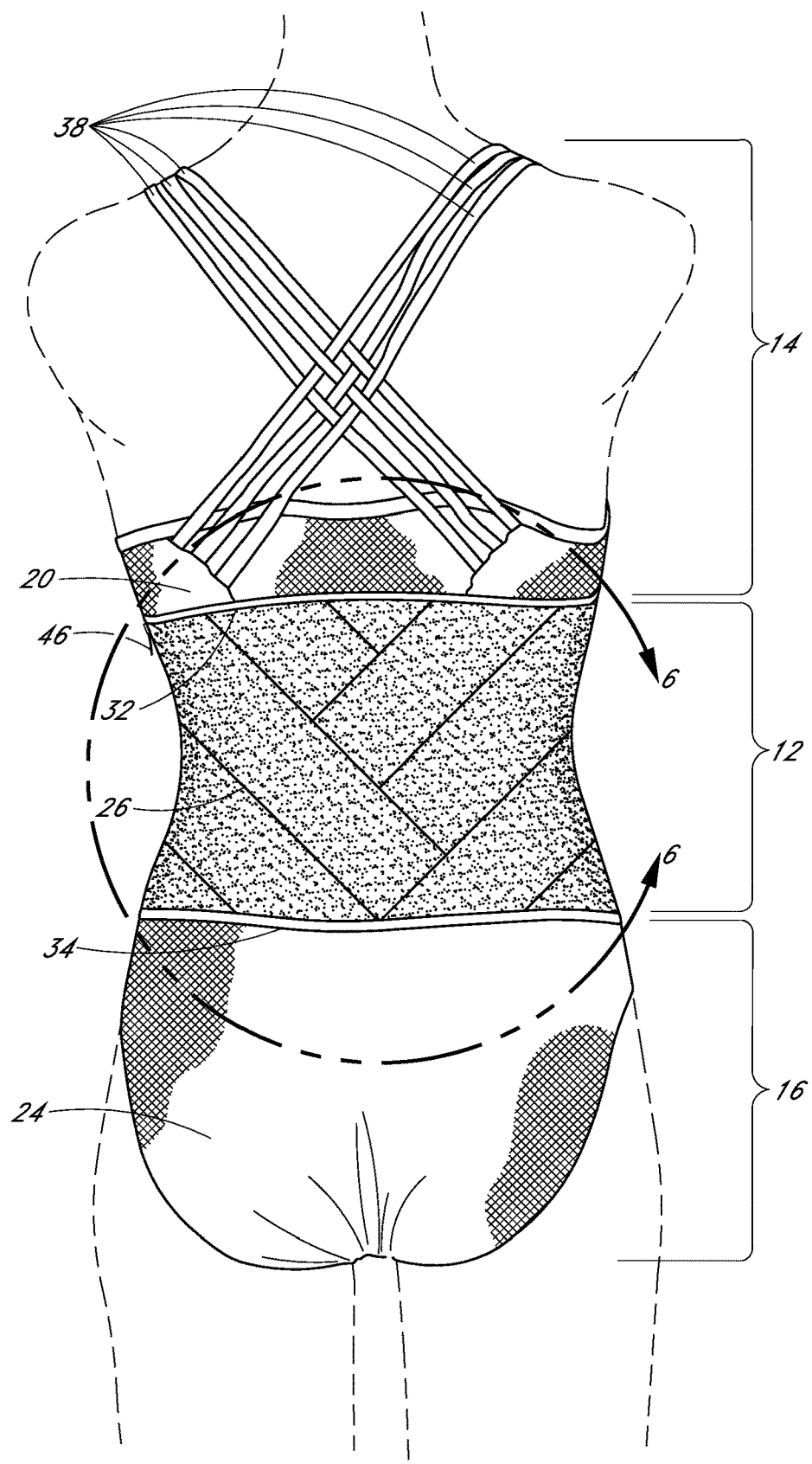
FIG. 9 is a back perspective view of the leotard from FIG. 7 showing an arrangement of the one or more panels of the compression system.

FIG. 7 is a front perspective view of another embodiment of a garment 10 having a zipper 46 in a compression system 12. FIG. 8 is a partial view of the garment from FIG. 7 showing the zipper 46. FIG. 9 is a back perspective view of the garment 10 from FIG. 7 showing an arrangement of the one or more panels 26 of the compression system 12 similar to the arrangement illustrated in FIG. 6.

Figure 10:
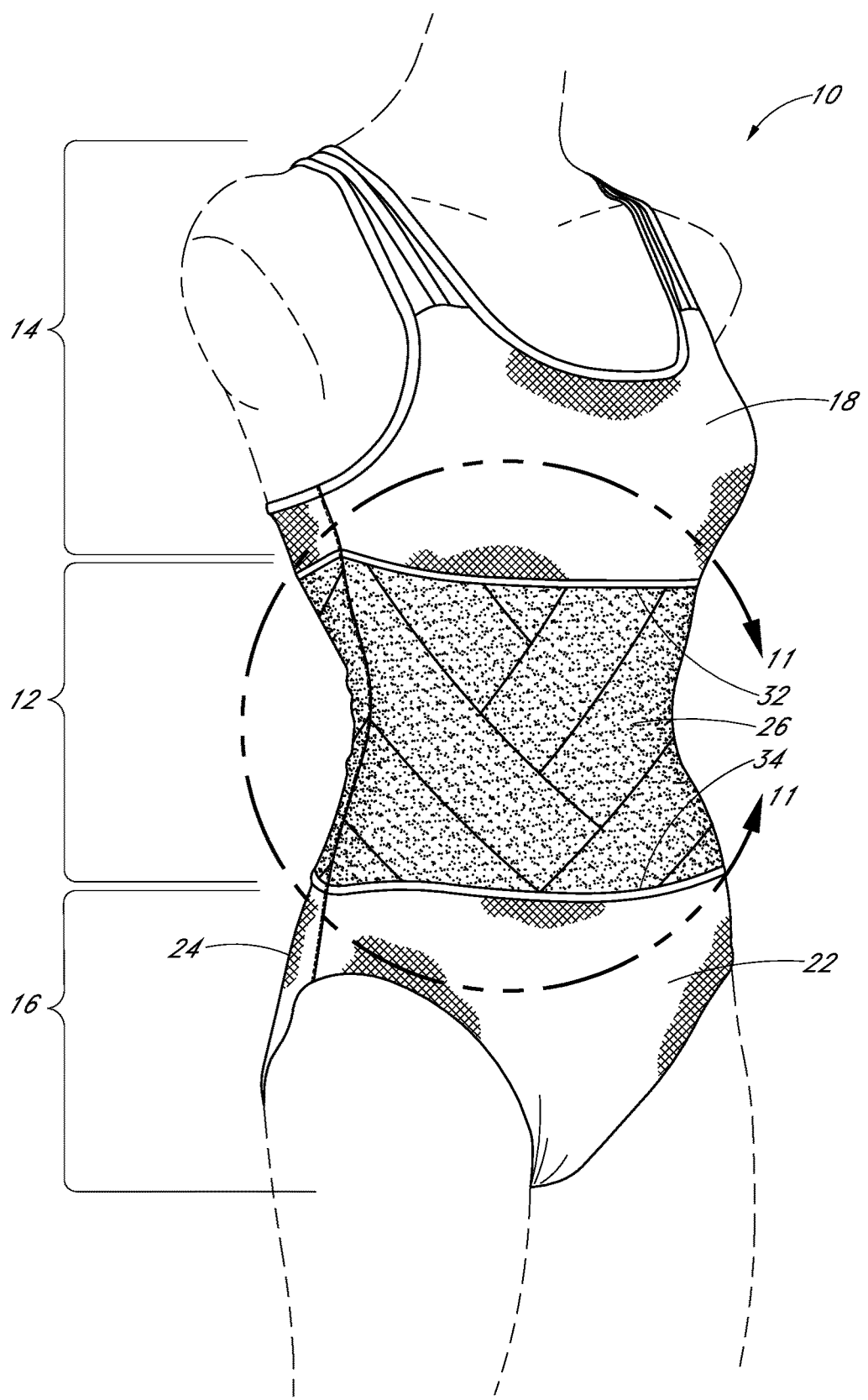
FIG. 10 is a front perspective view of another embodiment of a leotard having a compression system disposed around the waist of the user.
Figure 11:
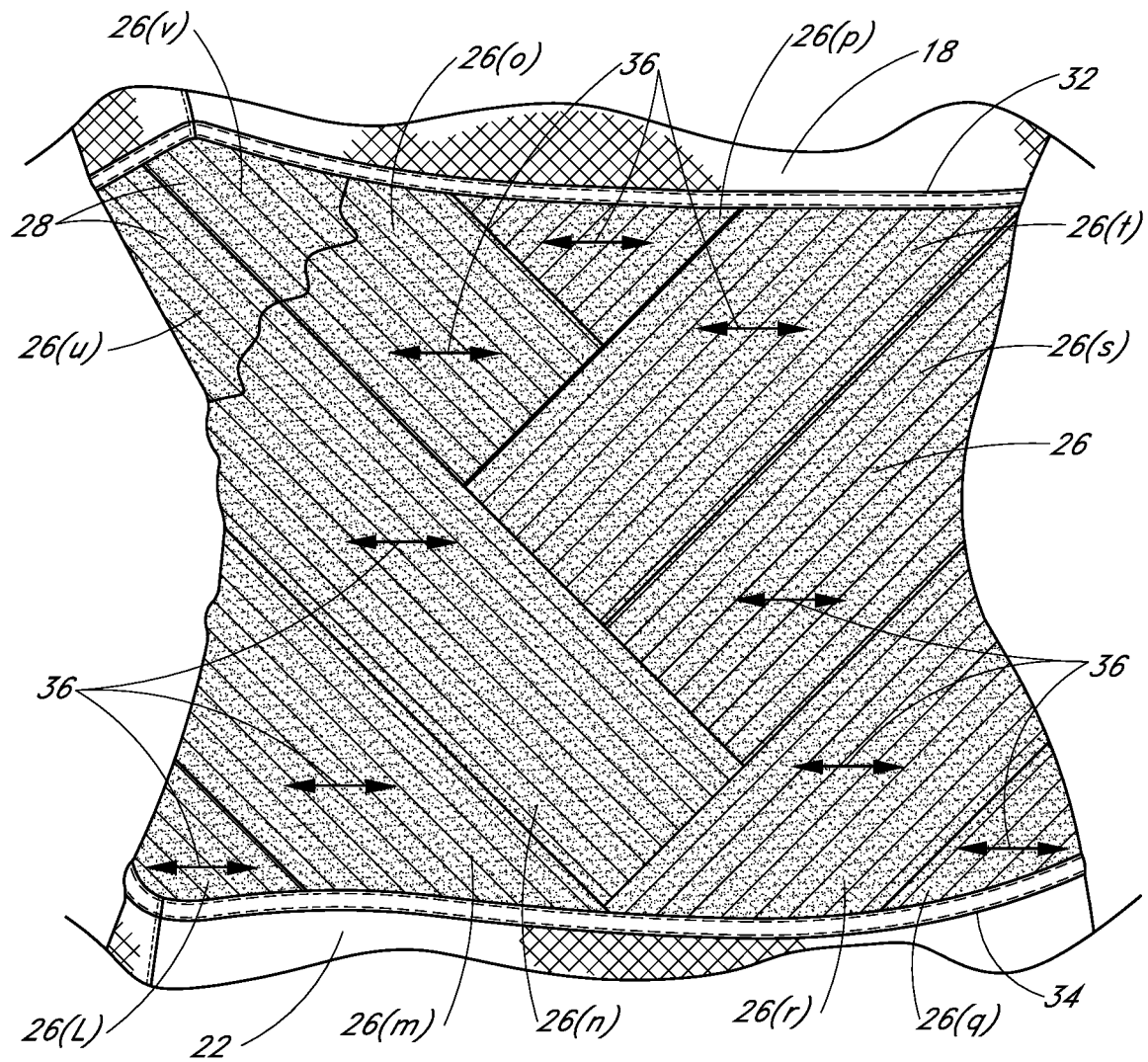
FIG. 11 is a partial view of the leotard from FIG. 10 showing the one or more panels of the compression material.
Figure 12:
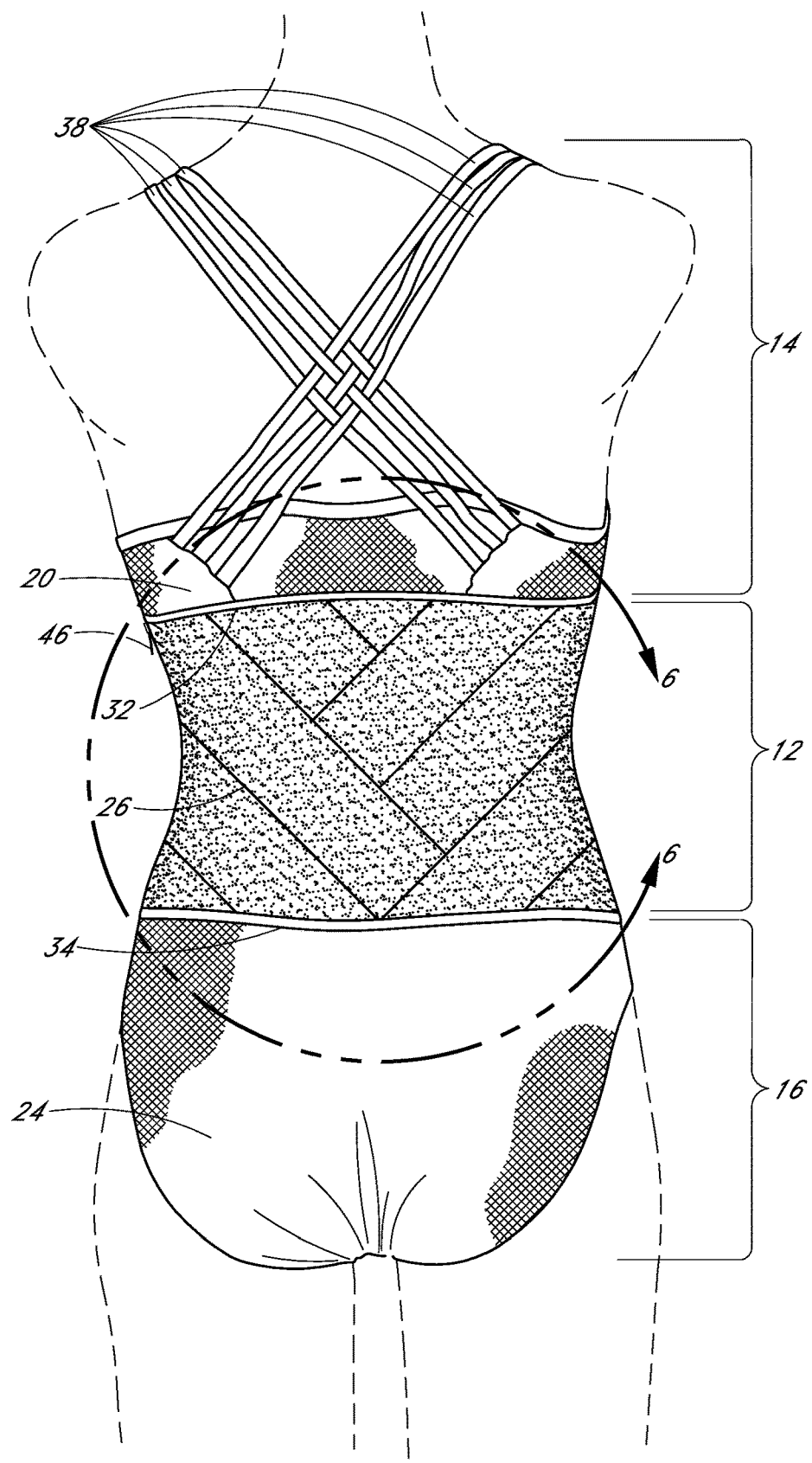
FIG. 12 is a back perspective view of the leotard from FIG. 10 showing an arrangement of the one or more panels of the compression system.

FIG. 10 is a front perspective view of another embodiment of a garment 10 having a compression system 12 disposed around the waist of the user. FIG. 11 is a partial view of the garment 10 from FIG. 10 showing one or more panels 26 of the compression material. FIG. 12 is a back perspective view of the garment 10 from FIG. 10 showing an arrangement of the one or more panels 26 of the compression system 12. The garment 10 illustrated in FIGS. 10-12 is similar to the garment 10 illustrated in FIGS. 4-6 except the arrangement of the one or more panels 26 on the front in FIG. 4 has been replaced with the arrangement of the one or more panels 26 on the back in FIG. 5.

As is illustrated by at least the embodiments disclosed in FIGS. 1-12, each of the upper and lower portions 14, 16 can comprise any number of panels 26, straps 38, etc. For example, each of the upper and lower portions 14, 16 can further comprise one or more panels 26 that entirely or partially overlap with another panel 26.

In certain embodiments, the upper and lower portions 14, 16 comprise a 4-way stretch fabric (e.g., warp knit tricot stretches in both directions, crosswise and lengthwise). In certain embodiments, the upper and lower portions 14, 16 comprise a 2-way stretch fabric (e.g., warp knit raschel stretches in both directions, width and length). An exemplary material for the upper portion 14 and the lower portion 16 is a tricot textile. In certain embodiments, the tricot textile comprises 81% nylon and 19% spandex. In certain embodiments, characteristics of the material for the upper portion 14 and the lower portion 16 can include a width stretch of 102 (+/−10%) and a length stretch of 136 (+/−10%). Of course this disclosure is not limited to the tricot textile as any other fabric can be used.

The garment 10 comprises at least one compression system 12 arranged to provide compression to a selected region of the user's body. In certain embodiments comprising more than one compression system 12, the compression systems 12 can be arrange to be adjacent to each other or separated by one or more panels located between the two compression systems 12. In certain embodiments, the compression system 12 is disposed between the upper portion 14 and the lower portion 16. In certain embodiments, the compression system 12 comprises a textile that provides a compression level greater than compression levels provided by the upper portion 14 and the lower portion 16. In certain embodiments, the compression system 12 provides a level of compression more than twice the level of compression provide by each of the upper portion 14 and the lower portion 16.

In certain embodiments, the compression system 12 extends entirely around the selected region of the user's body, such as, for example, the waist. In certain embodiments, the compression system 12 extends about only a portion of the selected region.

Each compression system 12 can comprise one or more layers with at least a portion of each layer comprising the one or more panels 26 of compression fabric. In certain embodiments, the one or more panels 26 comprise a medical grade textile. In certain embodiments, the one or more panels 26 are shaped, positioned, and sized within the garment 10 to provide the user a level of compression, for example, 10-20 mmHg, over the selected or targeted region of the user's body. In certain embodiments, the garment 10 incorporates multiple panels 26 with each panel 26 being directed to a variety of muscle groups of the user.

Embodiments of the garment 10 can be designed with low, medium, and high compression. As is illustrated by FIGS. 7-9, embodiments of the garment 10 can incorporate one or more zippers 46 or other closures to increase compression beyond what the one or more panels 26 alone would enable.

Embodiments of the garment 10 may also incorporate features such as ribs or seams that anchor a given panel 26 to the garment 10. In certain embodiments, reinforcement features can be incorporated into the garment 10 such as tapes or elements that do not stretch or stretch at a different rate than the panel 26 of compression fabric.

In certain embodiments, the one or more panels 26 are arranged end to end within a given layer to provide the compression to the selected region of the user's body. In certain embodiments, the one or more panels 26 are interspersed with other types of panels within any given layer. In this way in certain embodiments, the one or more panels 26 of compression fabric are active panels.

In certain embodiments, each of the one or more layers of the compression system 12 comprises a single panel 26. The single panel 26 can be formed into an annular shape when the panel 26 is woven. In this way, at least the compression system 12 portion of the garment 10 can be formed using seamless construction. For example, a band of the compression system 12 can be formed using seamless construction such that the band extends entirely circumferentially with no seam along the circumference. In other embodiments, the compression system 12 is formed into an annular shape during manufacture of the garment 10. For example, opposite ends of the panel 26 of the compression system 12 can be sewn together to form the annular shape.

In certain embodiments, the band formed by the compression system 12 extends circumferentially and wholly encompasses or surrounds the selected region of the user's body, such as the waist. In certain embodiments, a width of the band is constant around its circumference. For example, in certain embodiments, the width of the band is 6", 7", or 8". In certain embodiments, the width of the band varies around its circumference. For example, in certain embodiments, the width of the band varies from 6" to 8" depending on the specific circumferential locations being covered by the at least one compression system 12. As explained above, the incorporation of the at least one compression system 12 in the garment 10 can provide support and aid in muscular metabolism in joints (hips, shoulder and back) of athletes.

The at least one compression system 12 can comprise one or more of the layers. For example, in certain embodiments, the compression system 12 comprises two overlapping layers with at least a portion of each layer comprising at least one panel 26 of compression fabric. In certain embodiments, the compression system 12 comprise the inner layer 28 and the outer layer 30. In certain embodiments, the inner layer 28 and the outer layer 30 are connected or sewn together at only an upper edge 32 and a lower edge 34. In certain embodiments, the inner layer 28 and outer layer 30 separately contract and expand during use. For example, by only sewing or connecting the inner layer 28 to the outer layer 30 at the upper edge 32 and the lower edge 34, each layer is able to float over the other layer during use.

Methods for connecting the one or more panels 26 together or the inner and outer layers 28, 30 together can be by any means known to one of skill in the art, and include, but are not limited to, sewing, ultrasonic sealing, elastomeric bonding, heat bonding, etc. Furthermore, the at least one compression system 12 and parts thereof can employ VELCRO® (a hook and loop fastener) for attachment within the garment 10.

The individual panels 26, each having a seamless construction in both the width height directions, can be combined, e.g., during a cut-and-sewn process to form the compression system 12 with only a limited number of seams. In certain embodiments, a pair of panels 26 are each located in the compression system 12 and then joined together by stitching at their interface. In certain embodiments, minimizing the number of seams in the garment 10 can help to contribute to overall comfort and wearability.

In certain embodiments such as illustrated in FIG. 6, the inner layer 28 and the outer layer 30 are connected or sewn together at locations in addition to the upper edge 32 and the lower edge 34. For example, in certain embodiments, the one or more panels 26 (a)-(k) of the inner and outer layers 28, 30 are sewn together at one or more locations or regions between the upper edge 32 and the lower edge 34. For example, in certain embodiments, overlapping panels 26 from the inner and outer layers 28, 30 are sewn together along at least a portion of their outer circumference in a region between the upper edge 32 and the lower edge 34. Additional strength and stability to the garment 10 may be achieved by sewing or attaching together overlapping panels from different layers in regions between the upper edge 32 and the lower edge 34.

Figure 13:
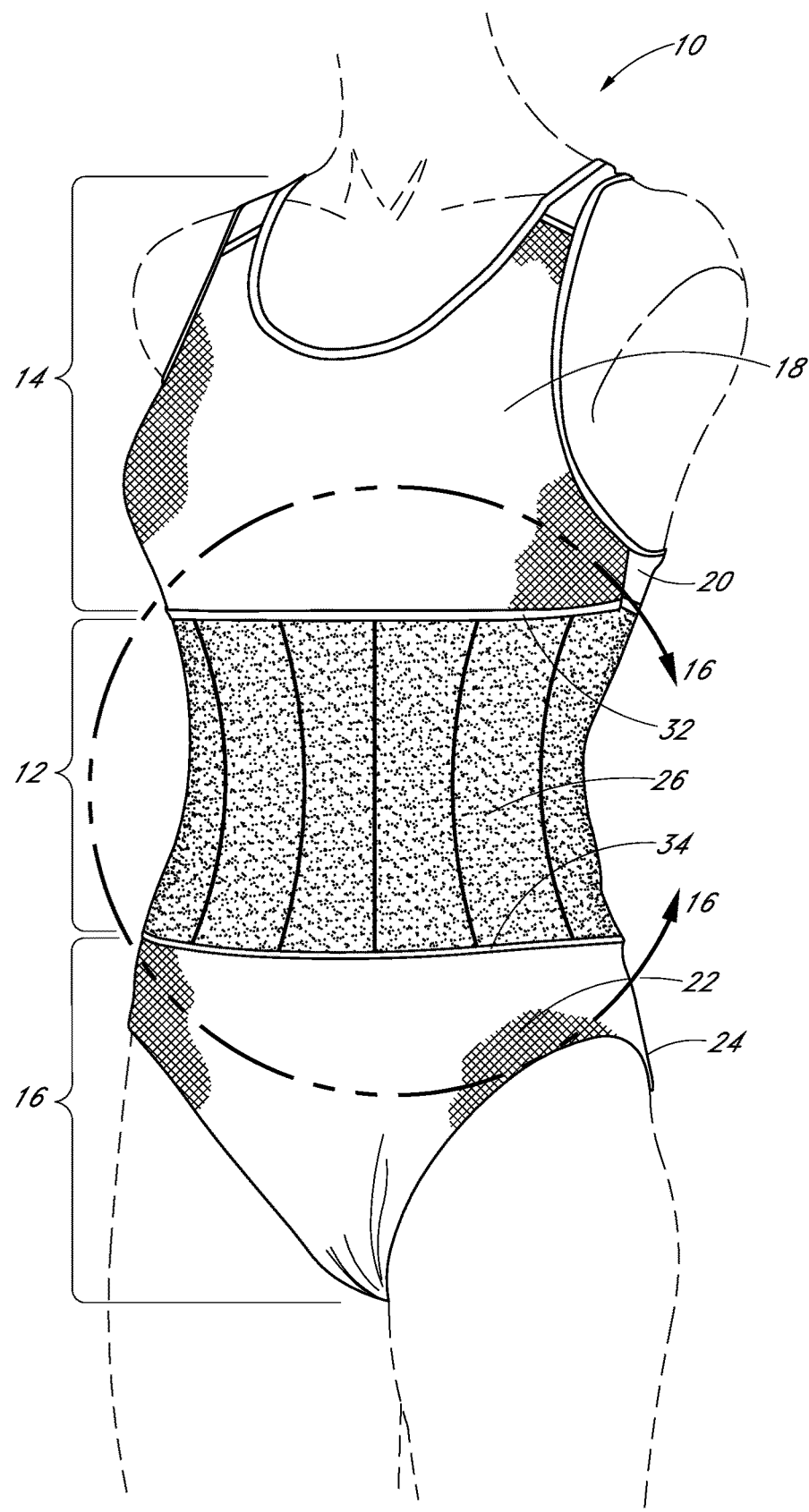
FIG. 13 is a front perspective view of another embodiment of a leotard having a compression system disposed around the waist of the user.
Figure 14:
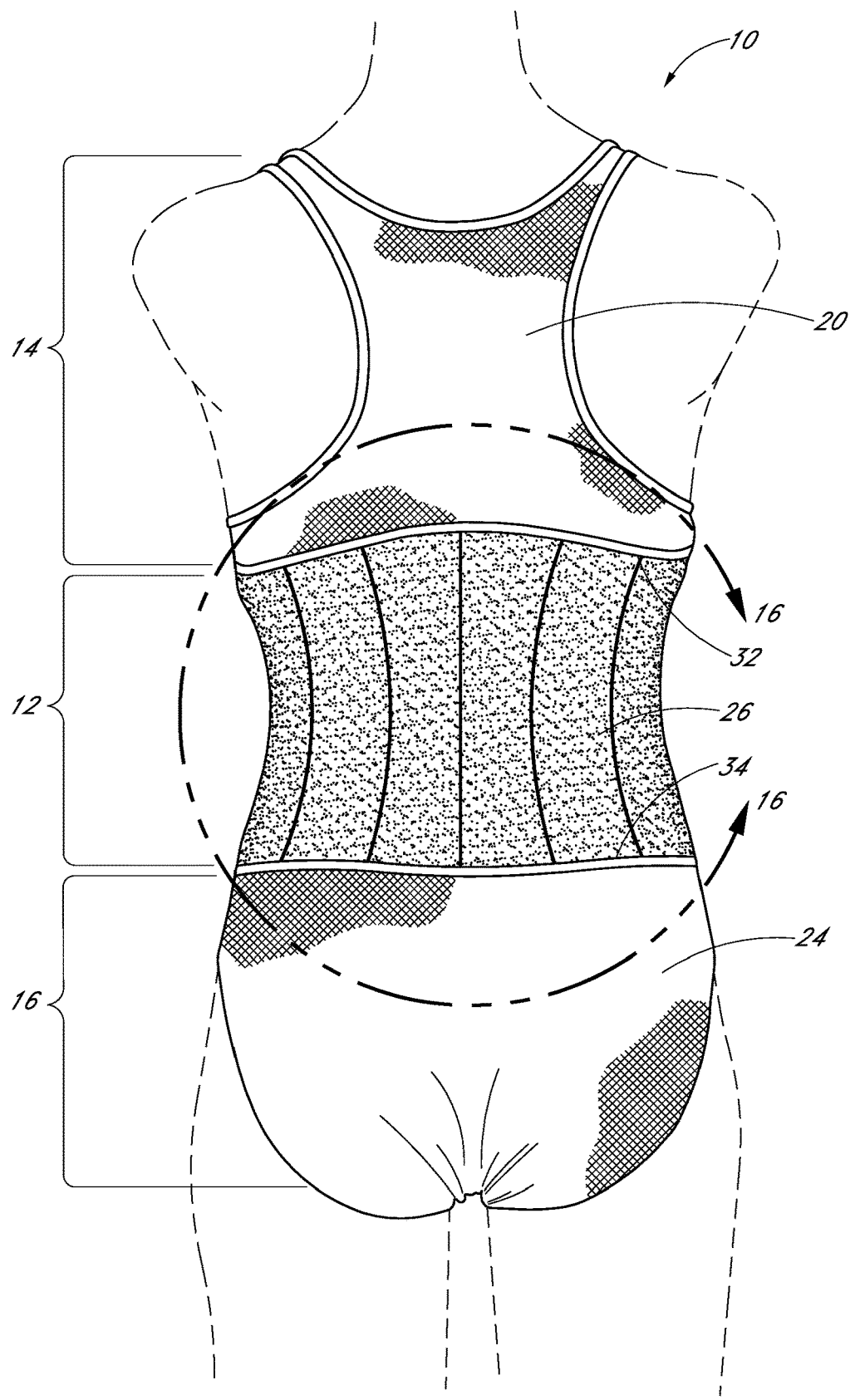
FIG. 14 is a back perspective view of the leotard from FIG. 13 showing an arrangement of the one or more panels of the compression system.
Figure 15:
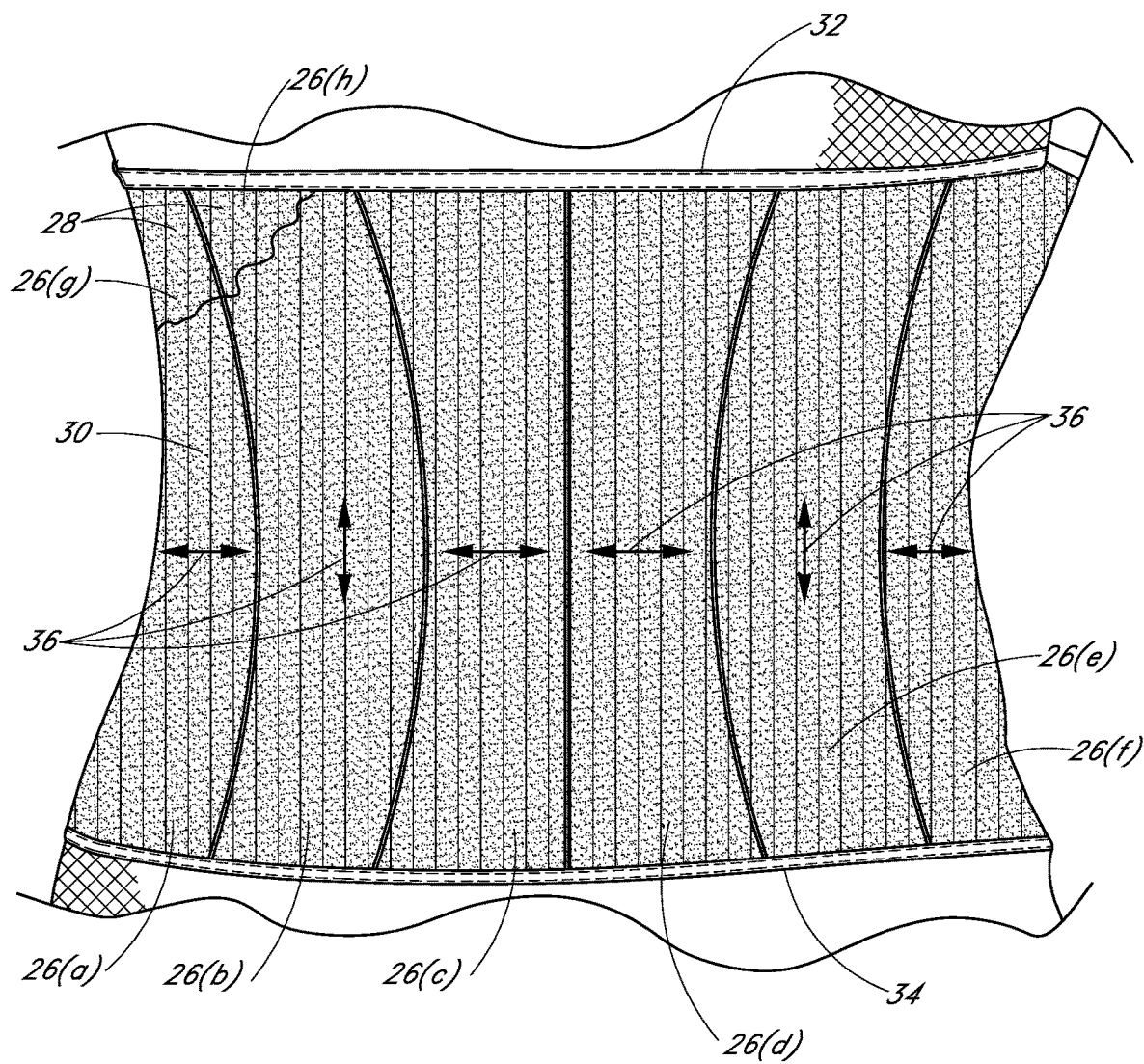
FIG. 15 is a partial view of the leotard from FIGS. 13 and 14 showing the one or more panels of the compression material.

FIG. 13 is a front perspective view of another embodiment of a garment 10 having a compression system 12 disposed around the waist of the user. FIG. 14 is a back perspective view of the garment 10 from FIG. 13 showing an arrangement of the one or more panels 26 of the compression system 12. FIG. 15 is a partial view of the garment 10 from FIGS. 13 and 14 showing the one or more panels 26 of the compression material arrange in a corset design. In this way, the each of the one or more panels 26 in the outer layer 30 are individually sewn to the one or more panels 26 in the inner layer 26. For example, panel 26 (a) from the outer layer 30 is sewn to panel 26 (g) from the inner layer 28.

A desired level of compression from the al. least one compression system 12 can be achieved by, for example, selecting compression fabric that has desirable characteristics and/or properties. For example, the level of compression can vary depending on, for example, the selected elastomeric yarn such as spandex, LYCRA®, ELASPAN®, elastane, etc., the selected percent weight of the elastomeric yarn, the degrees of stretch in the length and width, the elastomeric yarn Denier, and/or load. In certain embodiments, the one or more panels 26 have the following characteristics and/or properties: 8.50 oz/sq yard; 45% nylon; 55% spandex; Yarn 150/17 SD Nylon; Spandex Denier 140; Length stretch 85%; Width stretch 95%; and/or Load 15. Other suitable fibers or yarn include synthetic yarn or fibers formed, e.g., of polyester, nylon, or acrylic; natural yarn or fibers formed, e.g., of cotton or wool; and regenerate yarn or fibers, such as rayon. In certain embodiments, the gauge of the one or more panels 26 is 32.

In certain embodiments, the characteristics and/or properties of the compression fabric are selected so that the at least one compression system 12 provides compression of 12 mmHg, 8-15 mmHg, 15-20 mmHg, 20-30 mmHg, or any other value or range for the desired compression. In certain embodiments, the one or more panels 26 can be an easily stretched fabric having a first level of compression, such as 8-15 mmHg, which slightly restricts movement. In certain embodiments, the one or more panels 26 can be a harder to stretch fabric having a second level of compression, such as 15-20 mmHg. In certain embodiments, the one or more panels 26 can be a hard to stretch fabric having a third level of compression, such as 20-30 mmHg.

In certain embodiments, the degree of stretch (i.e., the degree of stretchability) provided by the at least compression system 12 is greater than the degree of stretch provided by the upper and lower portions 14, 16. For example, in certain embodiments, the at least one panel 26 comprises 45% nylon and 55% spandex which provides a greater degree of stretch than upper and lower portions that each comprise 81% nylon and 19% spandex.

The desired level of compression can also be achieved by selecting more than one layer of the compression fabric, selecting the orientation of the one or more panels 26 relative to the selected region of the user's body and/or other panels 26, and/or selecting an amount of overlap between panels 26 of multiple layers.

In embodiments that include at least the inner layer 28 and the outer layer 30, each layer 28, 30 can contribute to the overall compression provided by the compression system 12. In certain embodiments, the contribution to the compression value from each layer of the compression system 12 is equal. In certain embodiments, the contribution to the compression value from each layer of the compression system 12 is different.

In certain embodiments, selecting a specific orientation of the one or more panels 26 within the garment 10 can provide the desired level of compression. For example as is illustrated in at least FIGS. 3, 6, 11, and 15, the orientation of the one or more panels 26 within the garment 10, even when the panels 26 comprise a 4-way stretch fabric, can be selected based on a predominant 2-way stretch 36 direction of the panel 26. While the 4-way stretch fabric will stretch in all four directions, the 4-way stretch fabric can have a higher degree of stretch or a predominant stretch in one of the two 2-way directions. The one or more panels 26 can be oriented in the garment 10 taking into account each panel's 26 predominant 2-way stretch direction. For example, in certain embodiments, a panel 26 of the one or more panels 26 is located within the garment 10 so that the predominant 2-way stretch direction 36 of the panel 26 is parallel to a height direction of the user. In certain embodiments, a panel 26 of the one or more panels 26 is located within the garment 10 so that the predominant 2-way stretch direction 36 of the panel 26 is parallel to a width direction of the user. Of course the orientation of the panel 26 is not limited to being perpendicular or parallel to the height or width directions and can instead be arrange at any angle relative to the directions.

In certain embodiments, the one or more panels 26 of the inner layer 28 entirely or partially overlaps with another panel 26 of the outer lay 30. For example, in certain embodiments, the at least one compression system 12 can comprise a panel 26 of the inner layer 28 and a panel 26 of an outer layer 30. The panel 26 of the outer layer 30 can entirely or partially overlap the panel 26 of the inner layer 28.

Figure 16:
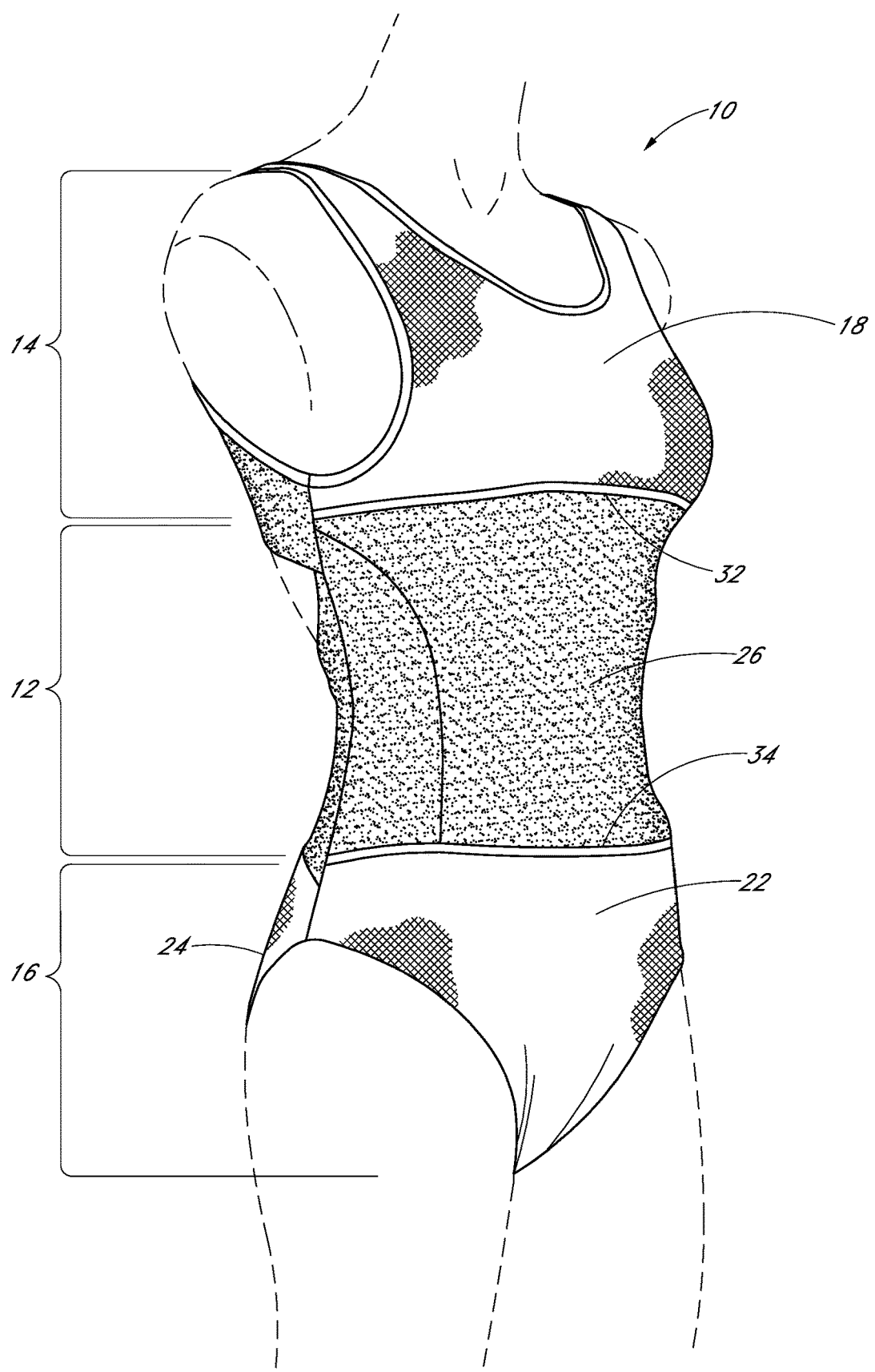
FIG. 16 is a front perspective view of another embodiment of a leotard having a compression system disposed around the waist of the user.
Figure 17:
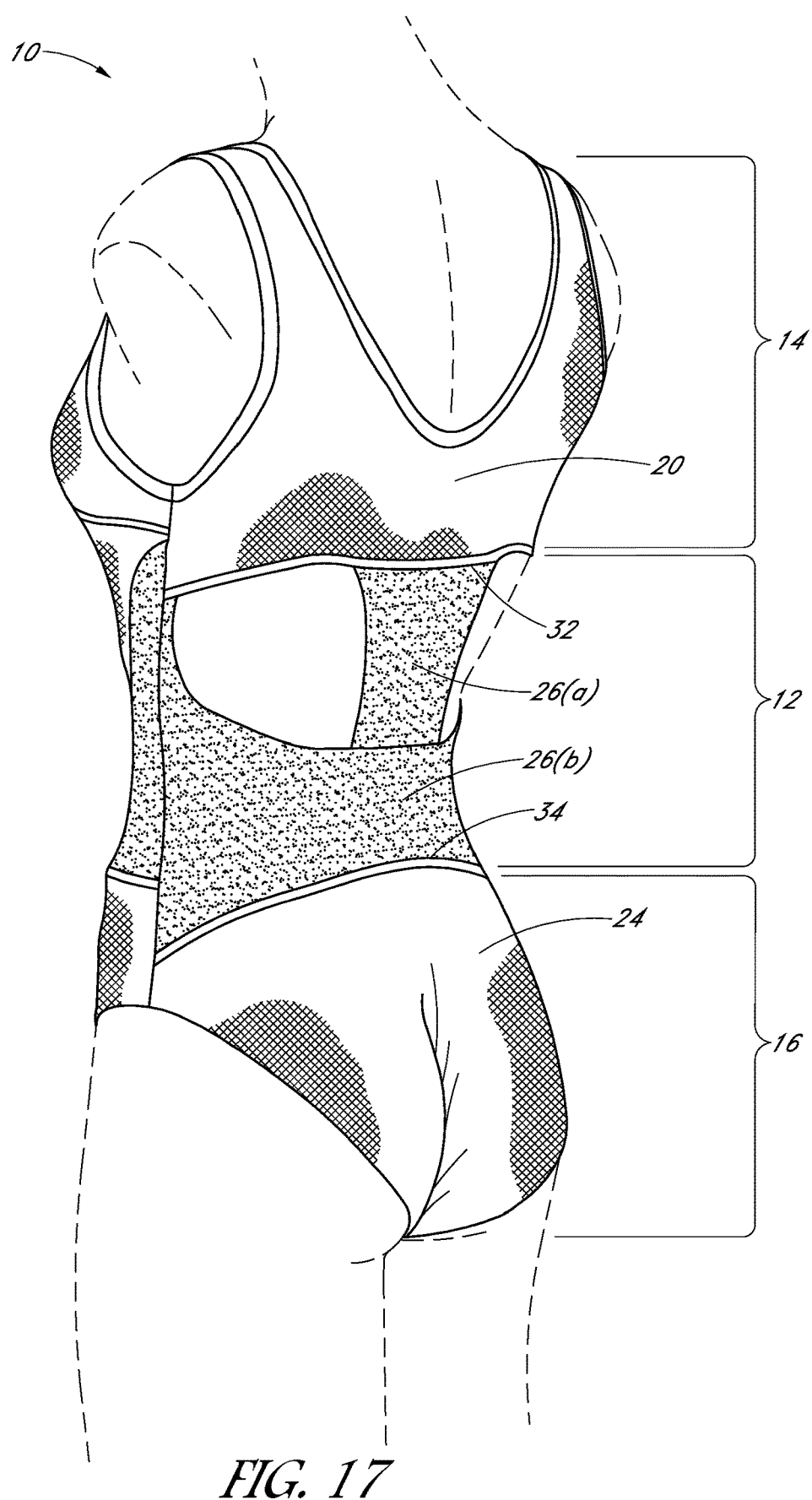
FIG. 17 is a back perspective view of the leotard from FIG. 16 showing an arrangement of the one or more panels of the compression system.

FIG. 16 is a front perspective view of another embodiment of a garment 10 having a compression system 12 disposed around the waist of the user. FIG. 17 is a back perspective view of the garment 10 from FIG. 16 showing an arrangement of the one or more panels 26 of the compression system 12 that includes at least a vertical panel 26 (a) and a horizontal panel 26 (b). In certain embodiments, the vertical panel 26 (a) and the horizontal panel 26 (b) may be free floating or sewn together.

Figure 18:
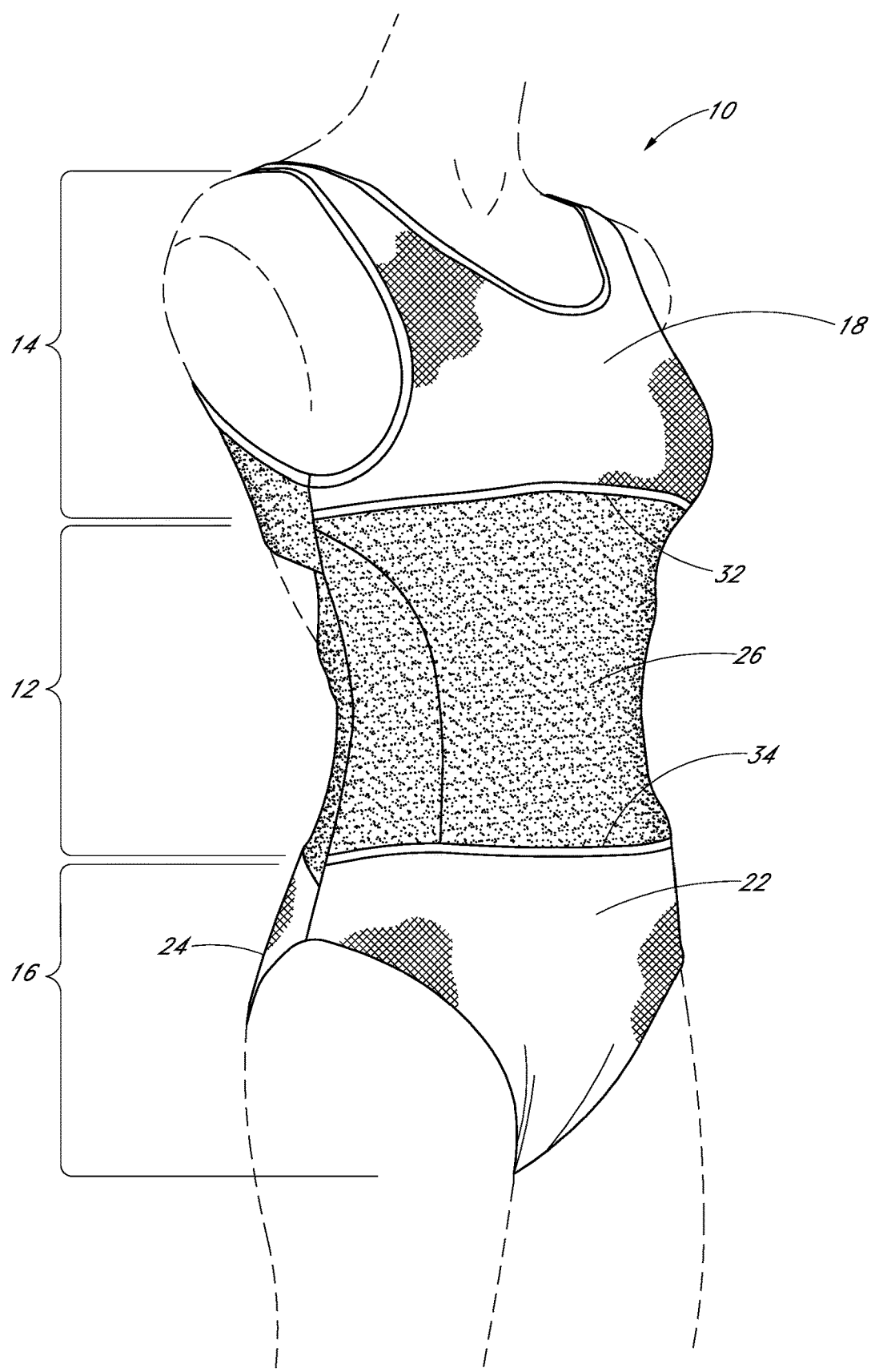
FIG. 18 is a front perspective view of another embodiment of a leotard having a compression system disposed around the waist of the user.
Figure 19:
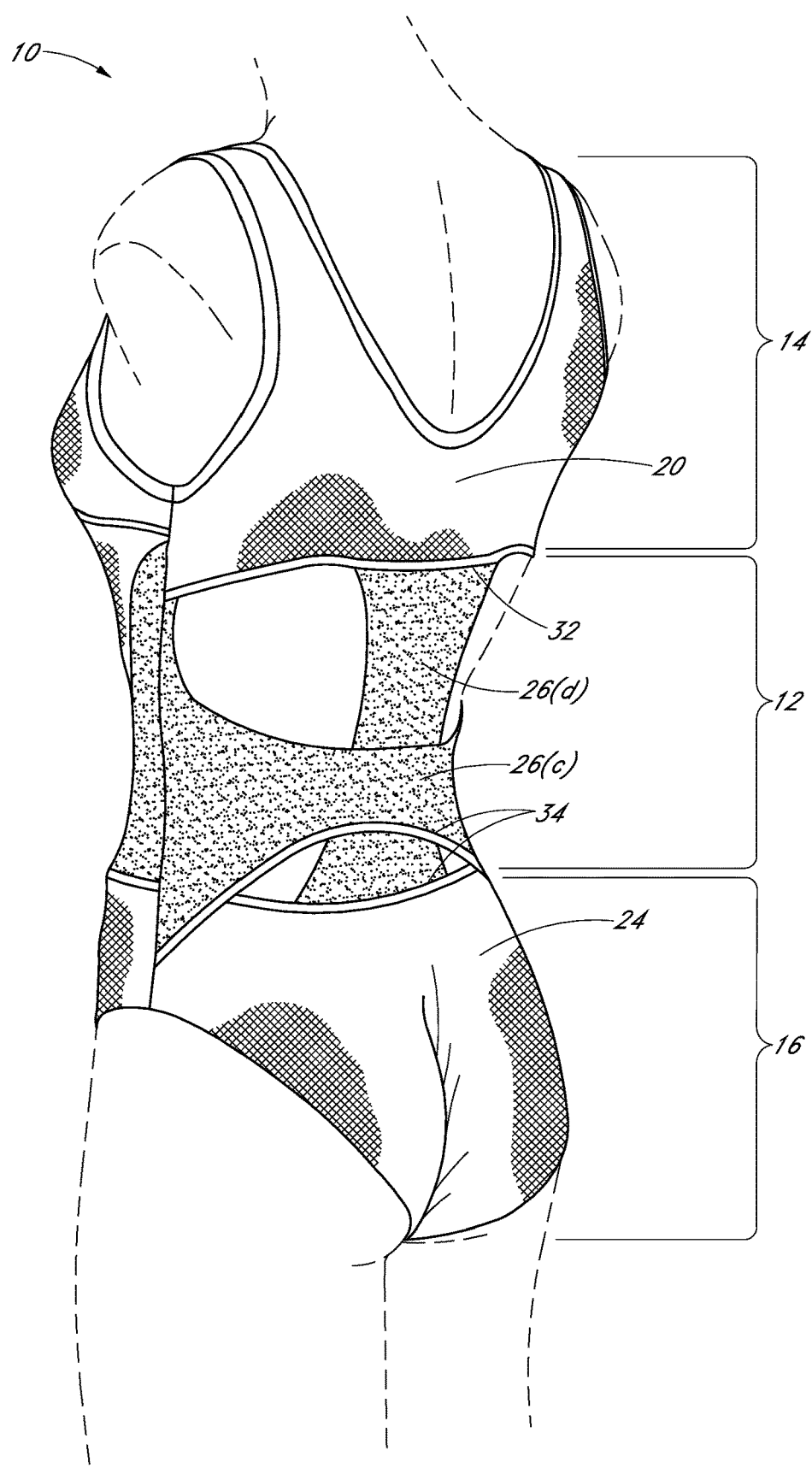
FIG. 19 is a back perspective view of the leotard from FIG. 18 showing an arrangement of the one or more panels of the compression system.

FIG. 18 is a front perspective view of another embodiment of a garment 10 having a compression system 10 disposed around the waist of the user. FIG. 19 is a back perspective view of the garment 10 from FIG. 18 showing an arrangement of the one or more panels 26 of the compression system 12 that includes at least a vertical panel 26 (d) and a horizontal panel 26 (c). In certain embodiments, the vertical panel 26 (d) and the horizontal panel 26 (c) may be free floating or sewn together.

Figure 20:
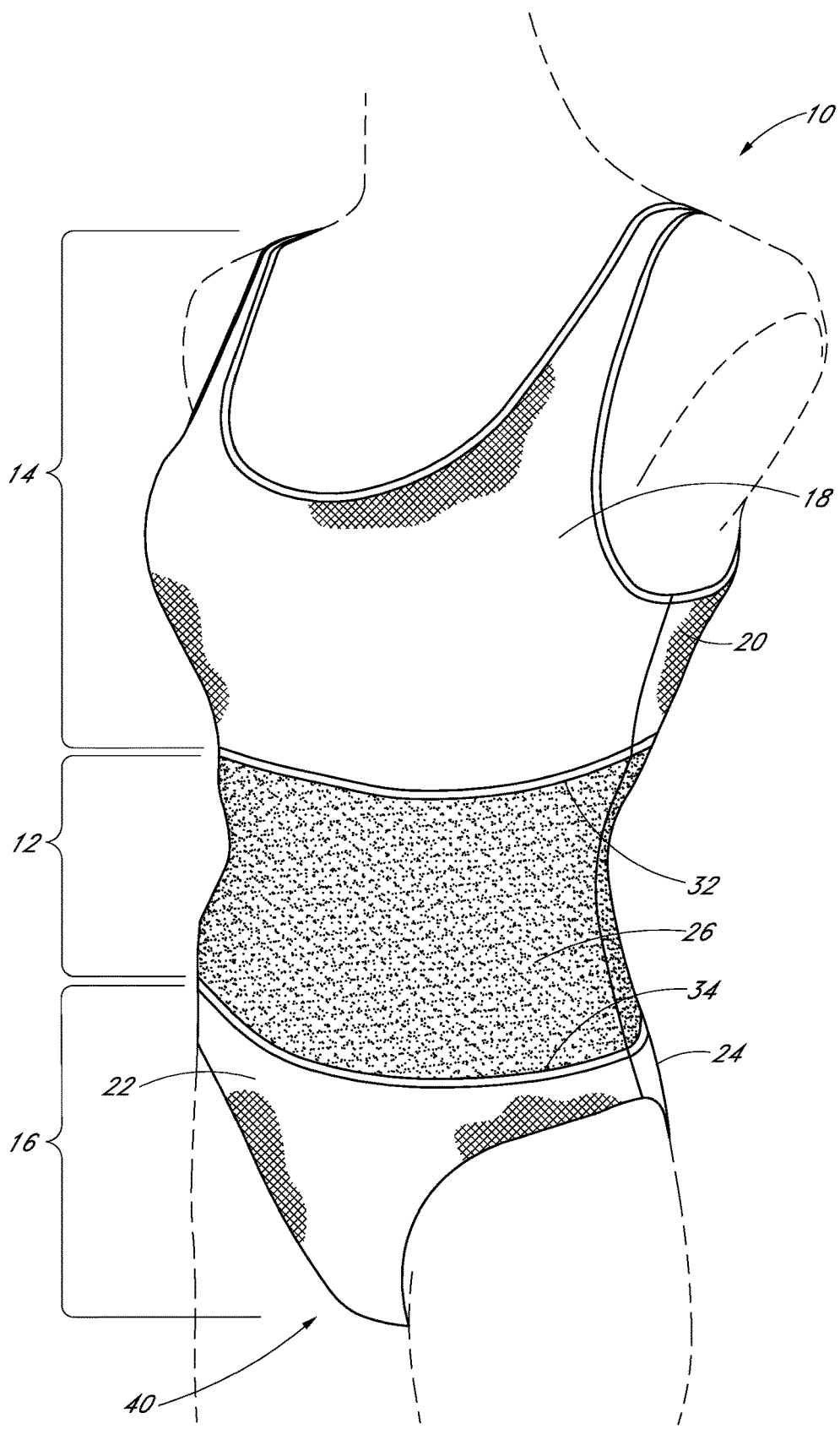
FIG. 20 is a front perspective view of a gym skin that has a compression system and is cut so as to be hidden by an outer garment.
Figure 21:
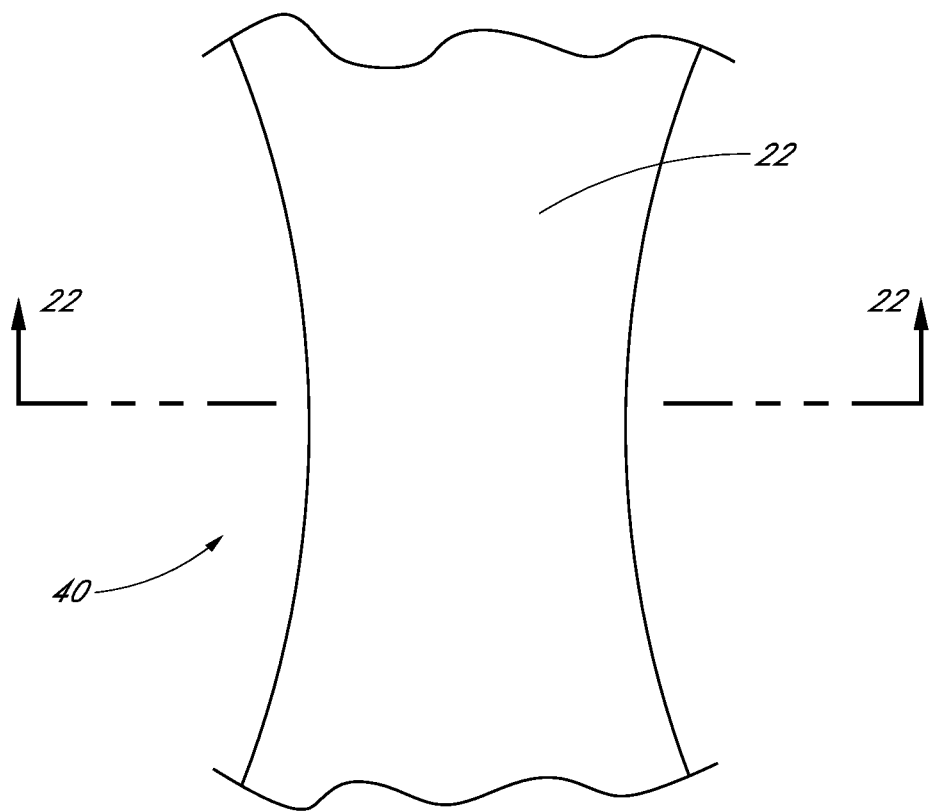
FIG. 21 is a partial view of the gym skin showing an absorber system in a crotch region of the gym skin.
Figure 22:
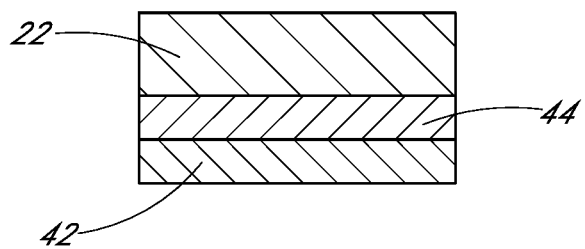
FIG. 22 is a cross-section view taken along lines 22-22 in FIG. 21.

FIG. 20 is a front perspective view of a garment 10 in the form of a gym skin. The garment 10 has a compression system 12 and is cut so as to be hidden by an outer garment. In certain embodiments, the garment 10 comprises an absorber system 40 in the crotch region. Any of the disclosed embodiments can include the absorber system 40.

The absorber system 40 can comprise a variety of materials, including, but not limited to, particles, fluid, foam, and any combination of these materials. In certain embodiments, the absorber system comprises an inner layer 42 of moisture wicking material and an outer layer 44 of protective lining. The inner layer 42 can comprise any material known to a person of skill in the art that transports moisture away and disperses it evenly throughout the inner layer 42 which results in a lack of moisture build-up and inhibits the growth of odor-causing bacteria.

The outer layer 44 can be made of any natural or synthetic fabric suitable for use in the crotch region of the garment 10, such as cotton, polyester, circular or warp knits, nylon, linen, rayon, and blends thereof. Preferably, the inner layer 42 and the outer layer 44 are anti-microbial, fabric technology that provides moisture transport, odor control and ease of cleaning all in one fabric. In certain embodiments, the inner layer 42 wicks moisture away from the user's body which provides a dryer and more comfortable feeling. In certain embodiments, the outer layer 44 is made of nylon and spandex. Of course, one of skill in the art will recognize that other materials may be used, such as cotton, polyester, and other acceptable fibers.

For expository purposes, the term "horizontal" as used herein is defined as a plane parallel to the plane or surface of the floor of the area in which the system being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated," and other such relational terms should be construed, unless otherwise noted, to include removable, moveable, fixed, adjustable, and/or releasable connections or attachments. The connections/attachments can include direct connections and/or connections having intermediate structure between the two components discussed.

The terms "approximately", "about", "generally" and "substantially" as used herein represent an amount close to the stated amount that still performs a desired function or achieves a desired result. For example, the terms "approximately", "about", "generally," and "substantially" may refer to an amount that is within less than 10% of the stated amount.

While the preferred embodiments of the present inventions have been described above, it should be understood that they have been presented by way of example only, and not of limitation. It will be apparent to persons skilled in the relevant art that various changes in form and detail can be made therein without departing from the spirit and scope of the inventions. Thus, the present inventions should not be limited by the above-described exemplary embodiments, but should be defined only in accordance with the following claims and their equivalents. Furthermore, while certain advantages of the inventions have been described herein, it is to be understood that not necessarily all such advantages may be achieved in accordance with any particular embodiment of the inventions. Thus, for example, those skilled in the art will recognize that the inventions may be embodied or carried out in a manner that achieves or optimizes one advantage or group of advantages as taught herein without necessarily achieving other advantages as may be taught or suggested herein.

What is claimed is:

1. A leotard configured to be worn by a user, comprising:
   an upper portion which is configured to be worn around at least a chest of the user;
   a lower portion which is configured to be worn over at least a crotch of the user; and
   a compression system disposed between and attaching the upper portion to the lower portion, wherein the compression system has a compression level greater than compression levels of the upper portion and the lower portion, and wherein the compression system comprises an inner layer and an outer layer, the inner layer and the outer layer comprising a plurality of inner panels and a plurality of outer panels, respectively, the plurality of inner panels and the plurality of outer panels comprising a 4-way stretch fabric, the 4-way stretch fabric having a first 2-way stretch direction and a second 2-way stretch direction perpendicular to the first 2-way stretch direction, the first 2-way stretch direction being a predominant 2-way stretch direction by having a higher degree of stretchability than the second 2-way stretch direction, wherein the predominant 2-way stretch direction of at least a first panel from the plurality of inner panels or the plurality of outer panels is different than the predominant 2-way stretch direction of at least a second panel from the plurality of inner panels or the plurality of outer panels so as to apply a level of compression.

2. The leotard of claim 1, wherein the compression level of the compression system is at least twice as great as the compression levels of the upper portion and the lower portion.

3. The leotard of claim 1, wherein the upper portion and the lower portion each comprise tricot fabric.

4. The leotard of claim 1, wherein the compression level of the compression system is 15-20 mmHg.

5. The leotard of claim 1, wherein the compression system is configured to be worn around a waist of the user.

6. The leotard of claim 1, wherein a width of the compression system is 7 inches.

7. The leotard of claim 1, wherein the compression system comprises a zipper configured to move between an open position and a closed position, a circumference of the compression system being greater when the zipper is in the open position than when the zipper is in the closed position.

8. The leotard of claim 1, wherein at least a region of the lower portion comprises an absorber system, the absorber system comprising an inner layer comprising a moisture wicking material and an outer layer comprising a protective lining.

9. A leotard configured to be worn by a user, comprising:
   an upper portion which is configured to be worn around at least a chest of the user and comprising spandex;
   a lower portion which is configured to be worn over at least a crotch of the user and comprising spandex; and
   a compression system disposed between and attaching the upper portion to the lower portion, the compression system having a percentage of spandex by weight that is at least twice as great as a percentage of spandex by weight in each of the upper portion and the lower portion, and wherein the compression system comprises an inner layer and an outer layer, the inner layer and the outer layer comprising a plurality of inner panels and a plurality of outer panels, respectively, the plurality of inner panels and the plurality of outer panels comprising a 4-way stretch fabric, the 4-way stretch fabric having a first 2-way stretch direction and a second 2-way stretch direction perpendicular to the first 2-way stretch direction, the first 2-way stretch direction being a predominant 2-way stretch direction by having a higher degree of stretchability than the second 2-way stretch direction, wherein the predominant 2-way stretch direction of at least a first panel from the plurality of inner panels or the plurality of outer panels is different than the predominant 2-way stretch direction of at least a second panel from the plurality of inner panels or the plurality of outer panels so as to apply a level of compression.

10. The leotard of claim 9, wherein the percentage of spandex by weight in the compression system is 55.

11. The leotard of claim 9, wherein the percentage of spandex by weight in the upper portion and the lower portion is 19.

12. The leotard of claim 9, wherein the compression system comprises 55% spandex by weight.

13. The leotard of claim 9, wherein the upper portion and the lower portion each comprise 19% spandex by weight.

14. A garment configured to be worn about at least a torso and a crotch of a user, comprising:
   an upper portion which is configured to be worn around at least a chest of the user;
   a lower portion which is configured to be worn over at least the crotch of the user; and
   a compression system disposed between the upper portion and the lower portion, the compression system configured to cover at least a portion of the torso and having a compression level of 10-20 mmHg, and wherein the compression system comprises an inner layer and an outer layer, the inner layer and the outer layer comprising a plurality of inner panels and a plurality of outer panels, respectively, the plurality of inner panels and the plurality of outer panels comprising a 4-way stretch fabric, the 4-way stretch fabric having a first 2-way stretch direction and a second 2-way stretch direction perpendicular to the first 2-way stretch direction, the first 2-way stretch direction being a predominant 2-way stretch direction by having a higher degree of stretchability than the second 2-way stretch direction, wherein the predominant 2-way stretch direction of at least a first panel from the plurality of inner panels or the plurality of outer panels is different than the predominant 2-way stretch direction of at least a second panel from the plurality of inner panels or the plurality of outer panels so as to apply a level of compression.

15. The garment of claim 14, wherein the compression system is configured to cover oblique muscles of the user.

16. The garment of claim 14, further comprising an upper panel attached to at least the upper portion, the upper panel being configured to be worn over at least portions of an upper back and a shoulder of the user.

17. The garment of claim 14, wherein a diameter of the compression system is 2-3 inches smaller than diameters of the upper portion and the lower portion, when in a relaxed configuration.

18. The garment of claim 14, wherein the compression system comprises a zipper configured to move between an open position and a closed position.

19. The garment of claim 14, wherein at least a region of the lower portion comprises an absorber system, the absorber system comprising an inner layer comprising a moisture wicking material and an outer layer comprising a protective lining.

20. The garment of claim 14, wherein each of the inner and outer layers comprises a textile having a compression level of 10-20 mmHg.

\* \* \* \* \*